US012714469B2

(12) United States Patent
Schroeder

(10) Patent No.: US 12,714,469 B2
(45) Date of Patent: Aug. 25, 2026

(54) SYSTEMS AND METHODS FOR FORMING PATIENT-SPECIFIC SPINAL RODS

(71) Applicant: K2M, Inc., Leesburg, VA (US)

(72) Inventor: Alex Schroeder, Columbia, MO (US)

(73) Assignee: Stryker Corporation, Portage, MI (US)

( * ) Notice: Subject to any disclaimer, the term of this patent is extended or adjusted under 35 U.S.C. 154(b) by 1213 days.

(21) Appl. No.: 17/054,343

(22) PCT Filed: May 10, 2019

(86) PCT No.: PCT/US2019/031731
§ 371 (c)(1),
(2) Date: Nov. 10, 2020

(87) PCT Pub. No.: WO2019/217824
PCT Pub. Date: Nov. 14, 2019

(65) Prior Publication Data

US 2021/0244447 A1 Aug. 12, 2021

Related U.S. Application Data

(60) Provisional application No. 62/670,606, filed on May 11, 2018.

(51) Int. Cl.
*A61B 17/70* (2006.01)
*A61B 17/00* (2006.01)
(Continued)

(52) U.S. Cl.
CPC .......... *A61B 17/7011* (2013.01); *A61B 34/10* (2016.02); *B33Y 80/00* (2014.12); (Continued)

(58) Field of Classification Search
None
See application file for complete search history.

(56) References Cited

U.S. PATENT DOCUMENTS 8,814,919 B2 8/2014 Barrus et al.
9,295,494 B2 3/2016 Strauss et al.
(Continued)

FOREIGN PATENT DOCUMENTS

CN 206443730 U * 8/2017
EP 3049011 A1 8/2016
(Continued)

OTHER PUBLICATIONS

Wang, An Orthopaedic Scraper, Aug. 2017, China National Intellectual Property Administration, pp. 1-4 (Year: 2017).*
(Continued)

*Primary Examiner* — Ryan F Pitaro
*Assistant Examiner* — Bernard E Cothran
(74) *Attorney, Agent, or Firm* — Lerner David LLP

(57) ABSTRACT

In one embodiment, a method using a computer system determines a length of a rod for use in spine correction surgery. With images of a patient, a segment of the spine requiring correction is identified along with first and second points at the ends of the segment. Then, a first size and a first position of a first circle are determined based on the image such that a portion of the first circle is generally aligned with a curve of the segment. A second circle with a different size and position is similarly determined based on the image. Both the first and second circles pass adjacent to or through the first point and the second point. A length of a portion of the second circle measured between the first and second points is then used to determine a rod length for a post-surgical spinal alignment.

20 Claims, 10 Drawing Sheets

(51) Int. Cl.
*A61B 34/10* (2016.01)
*B33Y 80/00* (2015.01)

(52) U.S. Cl.
CPC ............... *A61B 2017/00526* (2013.01); *A61B 2034/102* (2016.02); *A61B 2034/105* (2016.02)

(56) References Cited

U.S. PATENT DOCUMENTS

| | | | | |
|---|---|---|---|---|
| 9,801,662 | B2 | 10/2017 | Barrus | |
| 2010/0087864 | A1* | 4/2010 | Klein | A61B 17/7049 606/301 |
| 2014/0316420 | A1 | 10/2014 | Ballard et al. | |
| 2015/0100091 | A1 | 4/2015 | Tohmeh et al. | |

FOREIGN PATENT DOCUMENTS

| | | | |
|---|---|---|---|
| KR | 20090088778 | A * | 8/2009 |
| WO | 2015040552 | A1 | 3/2015 |

OTHER PUBLICATIONS

Ahn et al., Bone Density Measurement System which providing Menu Icon with Section Movement Facilitating and Method Thereof, Aug. 2009, Korean Patent Office, pp. 1-17 (Year: 2009).*

Langlotz, et al., "A Pilot Study on Computer-Assisted Optimal Contouring of Orthopedic Fixation Devices", Computer Aided Surgery, 4:6, Jan. 2010, pp. 305-313.

Legaye, et al., "Pelvic Incidence: A Fundamental Pelvic Parameter for Three-Dimensional Regulation of Spinal Sagittal Curves", European Spine Journal, vol. 7, Issue 2, May 1998, pp. 99-103.

Akbar, et al., "Use of Surgimap Spine in Sagittal Plane Analysis, Osteotomy Planning, and Correction Calculation", Apr. 2013, pp. 163-172.

Liu, et. al., "Main Thoracic Curve Adolescent Idiopathic Scoliosis: Association of Higher Rod Stiffness and Concave-Side Pedicle Screw Density With Improvement in Sagittal Thoracic Kyphosis Restoration", Journal Neurosurgery Spine, vol. 22, Mar. 2015, pp. 259-266.

Poster Presentations, International Meeting on Advanced Spine Techniques (IMAST), program held Jul. 2007, 31 pages.

Roussouly, et. al., "Pre- and Post-Operative Sagittal Balance in Idiopathic Scoliosis: A Comparison Over the Ages of Two Cohorts of 132 Adolescents and 52 Adults", European Spine Journal, Mar. 2013, (Suppl 2), pp. 203-215.

Aurouer, et. al., "Computerized Preoperative Planning for Correction of Sagittal Deformity of the Spine", Surg Radiol Anat, Jul. 2009, pp. 1-12.

Luk, et. al., "Coupling Between Sagittal and Frontal Plane Deformity Correction in Idiopathic Thoracic Scoliosis and Its Relationship With Postoperative Sagittal Alignment", Spine, vol. 35, No. 11, May 2010, pp. 1158-1164.

Monazzam, et. al., "Multicenter Comparison of the Factors Important in Restoring Thoracic Kyphosis During Posterior Instrumentation for Adolescent Idiopathic Scoliosis", Spine Deformity 1, Jun. 2013, pp. 359-364.

Cidambi, et. al., "Postoperative Changes in Spinal Rod Contour in Adolescent Idiopathic Scoliosis", Spine vol. 37, No. 18, Aug. 2012, pp. 1566-1572.

Demura, et. al., "Maintenance of Thoracic Kyphosis in the 3D Correction of Thoracic Adolescent Idiopathic Scoliosis Using Direct Vertebral Derotation", Spine Deformity 1, Jan. 2013, pp. 46-50.

Partial International Search Report for Application No. PCT/US2019/031731, mailed Sep. 3, 2019; 3 pages.

* cited by examiner

SYSTEMS AND METHODS FOR FORMING PATIENT-SPECIFIC SPINAL RODS

CROSS-REFERENCE TO RELATED APPLICATIONS

This application is a national phase entry under 35 U.S.C. § 371 of International Application No. PCT/US2019/031731, filed May 10, 2019, which claims the benefit of the filing date of U.S. Provisional Patent Application No. 62/670,606 filed May 11, 2018, the disclosures of which are hereby incorporated by reference herein in their entirety.

BACKGROUND OF THE INVENTION

A wide-variety of surgical devices and software are being developed and used to perform various orthopaedic surgical procedures. In many spine surgeries, software is used in pre-surgical planning and devices are used to surgically correct the alignment of a patient's spine so that the head is oriented over the pelvis in the axial, coronal, and sagittal planes. Specifically, software is used in conjunction with medical images (e.g., X-ray, Computed Tomography, or Magnetic Resonance Imaging images) to assess the alignment and/or malalignment of the spine from a segmental (individual vertebrae), regional (cervical, thoracic, lumbar, or pelvic), and global spinal perspective. Examples include cervical lordosis, thoracic kyphosis (TK), lumbar lordosis (LL), pelvic incidence (PI), pelvic tilt (PT), and sacral slope (SS). Surgical devices are used to attach to individual vertebrae—and with the use of various tools and connectors—change the alignment of the vertebrae with respect to one another to correct malalignment and achieve a better alignment.

Some software allows a clinician to identify relevant landmarks on an X-ray image of a patient's spine and simplifies the generation of the measures needed to assess alignment. Based on these baseline measures, the software can generate an optimal pattern of alignment for a specific patient. The software then allows the clinician to apply surgical corrections such as osteotomies and the use of interbody (between the vertebrae) fusion devices and simulate the result of those corrections to generate the desired post-surgical alignment. Once a desired alignment is achieved within the software, measures can be exported to generate a template or spinal implant that matches the simulated correction. Current methods, however, neither incorporate the changes in the shape of the spinal implants (e.g., rods) that occur when forces of correction are applied, nor do they account for the change in the relative length of the spine that also occurs.

For example, in some known systems, angular measures are used to describe the position of one vertebra in relation to another as an attempt to describe the shape of the spine. In these systems, a line parallel to the superior vertebral endplate of an upper vertebra is intersected with a line parallel to the inferior vertebral endplate of a lower vertebra to generate an angular measure representing the relative position of the spine between the two vertebrae. This is referred to as a Cobb angle. This information is used to generate the contour of the rod to be used in the surgery. However, these systems lack the ability to describe or measure the shape other than the relationship of the endplates of the two vertebrae, to generate a length from the measure, or to incorporate changes in length that occur as the relative position of the vertebrae change from the realignment in three anatomical planes. This can lead to errors in rod length, shape, and inability to achieve a proper spinal alignment in the patient.

Furthermore, current methods cannot predict an optimal shape of the implant when surgical corrections are not used to achieve the correct alignment and when the shape of the spinal rod is the primary correcting determinant.

Thus, a need exists for improved methods of determining a length of rod used in spinal correction surgery and also for spinal rods with improved fit and function when used in spinal correction surgery.

BRIEF SUMMARY OF THE INVENTION

In some aspects, the present disclosure features systems and methods that determine the appropriate pre-surgical shape of spinal rods that accounts for changes in the lengths of the spine (e.g., when a deformity is reduced) and shapes of spinal rods (when forces are applied to the implanted spinal rods) and aid in selecting the appropriate stiffness and elastic properties of the spinal rods. Those changes in the lengths are accounted for by a geometric algorithm that uses the radii of circles to convert from the angular measures that may be generated from software, along with stiffness characteristics of the patient's deformity, to determine the lengths and shapes of the spinal rods.

In one aspect, the present disclosure relates to a method of determining a length of a rod for use in spine correction surgery using a system with a processor and a memory. In one embodiment the method includes steps of: identifying a segment of the spine requiring correction using an image of the spine stored in the memory, the segment including a first point at a first end of the segment and a second point at a second end of the segment; determining a first size and a first position of a first circle based on the image by using the processor such that a portion of the first circle (e.g., an arc) is generally aligned with a curve of the segment and the first circle passes adjacent to or through the first point and the second point; modifying the first circle to define a second circle by using the processor, the second circle having a second size and a second position based on the image such that the second circle passes adjacent to or through the first point and the second point, a portion of the second circle (e.g., an arc) representing a post-surgical alignment of the segment; measuring, by the processor, a length of the portion of the second circle; and using the length of the portion of the second circle to determine the length of the rod where the rod is used in conjunction with pedicle screws to correct the spine.

In some embodiments, the method may include steps of: identifying a second segment of the spine requiring correction including a third point at a first end of the second segment and a fourth point at a second end of the second segment; establishing a third circle based on the image using the processor such that a portion of the third circle coincides with a curve of the second segment and the third circle passes adjacent to or through the third point and the fourth point, the second circle having a third size and a third position on the image; and modifying the second circle to define a fourth circle by using the processor, the fourth circle having a fourth size and a fourth position on the image such that the modified first circle passes adjacent to or through the third point and the fourth point.

In some embodiments, the points may be determined so that one of the first point and the second point is the same as one of the third point and the fourth point. In some embodiments, prior to modifying the second circle, the first circle and the second circle may share a common tangent. In some embodiments, the method may include modifying one of the second circle and the fourth circle so that each of the respective circles, as modified, share a common tangent. In some embodiments, the first circle may have a radius with a first size and the curve of the segment may have a radius with a second size, the first size being within 10% of the second size. In some embodiments, the post-surgical alignment may be determined by establishing an endpoint final post-surgical alignment and adding 15-25% to an angle representing the endpoint final post-surgical alignment. In some embodiments, the method may include placing the rod intraoperatively, the rod length being determined based on the post-surgical alignment. The rod, once secured to the spine, may be more closely aligned with the endpoint post-surgical alignment than the post-surgical alignment. In some embodiments, determining the first size and the first position of the first circle may involve aligning the first circle along a path passing through posterior sides of consecutive vertebrae of the spine. In some embodiments, the first point may be located at vertebra T1, T2, T3 or T4 and the second point may be located at vertebra T12, L1 or L2. In some embodiments, the third point may be located at vertebra T12, L1 or L2 and the fourth point may be located at vertebra L5, S1 or S2. In some embodiments, the image may capture the sagittal plane or the coronal plane. In some embodiments, the image may be an x-ray image.

In some embodiments, a first circle may have a radius that is representative of the existing curve of the spinal segment and a second radius that represents the post-surgical curve of the spinal segment. In some embodiments, the post-surgical alignment may be determined by establishing an endpoint final post-surgical alignment and adding an additional multiplier to allow for changes that occur from the forces of the corrective surgery.

In another aspect, the present disclosure relates to a method of determining a curvature of a rod for use in spine correction surgery using a system with a processor and a memory. In one embodiment, the method includes steps of: identifying a segment of the spine requiring correction using an image of the spine stored in the memory, the segment including a first point at a first end of the segment and a second point at a second end of the segment; determining a first size and a first position of a first circle based on the image using the processor such that a portion of the first circle is generally aligned with a curve of the segment and the first circle passes adjacent to or through the first point and the second point; modifying the first circle to define a second circle using the processor, the second circuit having a second size and a second position based on the image such that the second circle passes adjacent to or through the first point and the second point, a portion of the second circle representing a post-surgical alignment of the segment adjusted to compensate for an expected loss of contour when the rod is attached to the spine; measuring, by the processor, an angle between a first radial line extending between a center of the second circle and the first point and a second radial line extending between the center of the second circle and the second point; and using the angle and a radius of the second circle to determine a curvature of the segment.

In some embodiments, the expected loss of contour may be based on at least one of the material properties of the rod, the shape of the rod and the size of the rod. In some embodiments, the expected loss of contour may be within a range of 15% to 30% of the angle. In some embodiments, determining the first size and the first position of the first circle may involve aligning the first circle along a path passing through posterior sides of consecutive vertebrae of the spine.

In another aspect, the present disclosure relates to a method of making a spinal rod. In one embodiment, the method includes steps of: identifying a segment of the spine requiring correction using an image of the spine, the segment including a first point at a first end of the segment and a second point at a second end of the segment; determining a first size and a first position of a first circle based on the images such that a portion of the first circle generally aligns with a curve of the segment and the first circle passes adjacent to or through the first point and the second point; modifying the first circle to define a second circle having a second size and a second position based on the image such that the modified first circle passes adjacent to or through the first point and the second point, a portion of the second circle representing a post-surgical alignment of the segment; and forming the spinal rod to have a length based on a length of the portion of the second circle.

In some embodiments, the method may include selecting a material for use in forming the spinal rod. In some embodiments, the method may include selecting a rod shape from the group consisting of a cylinder, a partial I-beam, and an omega shape.

In yet another aspect, the present disclosure relates to a spinal rod structure. In one embodiment, the spinal rod structure includes a body with a length sufficient for use in a spinal deformity correction procedure. The length of the body is determined by: identifying a segment of the spine requiring correction using an image of the spine, the segment including a first point at a first end of the segment and a second point at a second end of the segment; determining a first size and a first position of a first circle based on the images such that a portion of the first circle (e.g., an arc) is generally aligned with a curve of the segment and the first circle passes adjacent to or through the first point and the second point; and modifying the first circle to define a second circle having a second size and a second position on the image such that the second circle passes adjacent to or through the first point and the second point, a portion of the second circle (e.g., an arc) representing a post-surgical alignment of the segment. The length of the spinal rod is commensurate with the portion of the second circle and is determined based on an angle between radial lines to each of the first point and the second point from a center of the second circle and either the radius of the second circle or a chord between the first point and the second point.

In some embodiments, the body may have a curvature determined based on the shape of the portion of the second circle.

In another aspect, the present disclosure relates to a method of determining a length of a rod for use in spine correction surgery using a system with a processor and a memory. The method includes: identifying a segment of the spine requiring correction using an image of the spine stored in the memory, the segment including a first point at a first end of the segment and a second point at a second end of the segment; determining a first size and a first position of a first geometric shape based on the image by using the processor such that a portion of the first geometric shape is generally aligned with a shape of the segment and the first geometric shape passes adjacent to or through the first point and the second point; modifying the first geometric shape to define a second geometric shape by using the processor, the second geometric shape having a second size and a second position based on the image such that the second geometric shape passes adjacent to or through the first point and the second point, a portion of the second geometric shape representing a post-surgical alignment of the segment; measuring, by the processor, a length of the portion of the second geometric shape; and using the length of the portion of the second geometric shape to determine the length of the rod where the rod is used in conjunction with pedicle screws to correct the spine.

In some embodiments, the image may be a three-dimensional image. In some embodiments, the image may include structure of the spine in the sagittal plane, the coronal plane, and the transverse plane.

In some embodiments, the geometric shape may be elliptical. In some embodiments, the geometric shape may be oval. In some embodiments, the geometric shape may be a three-dimensional curve.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
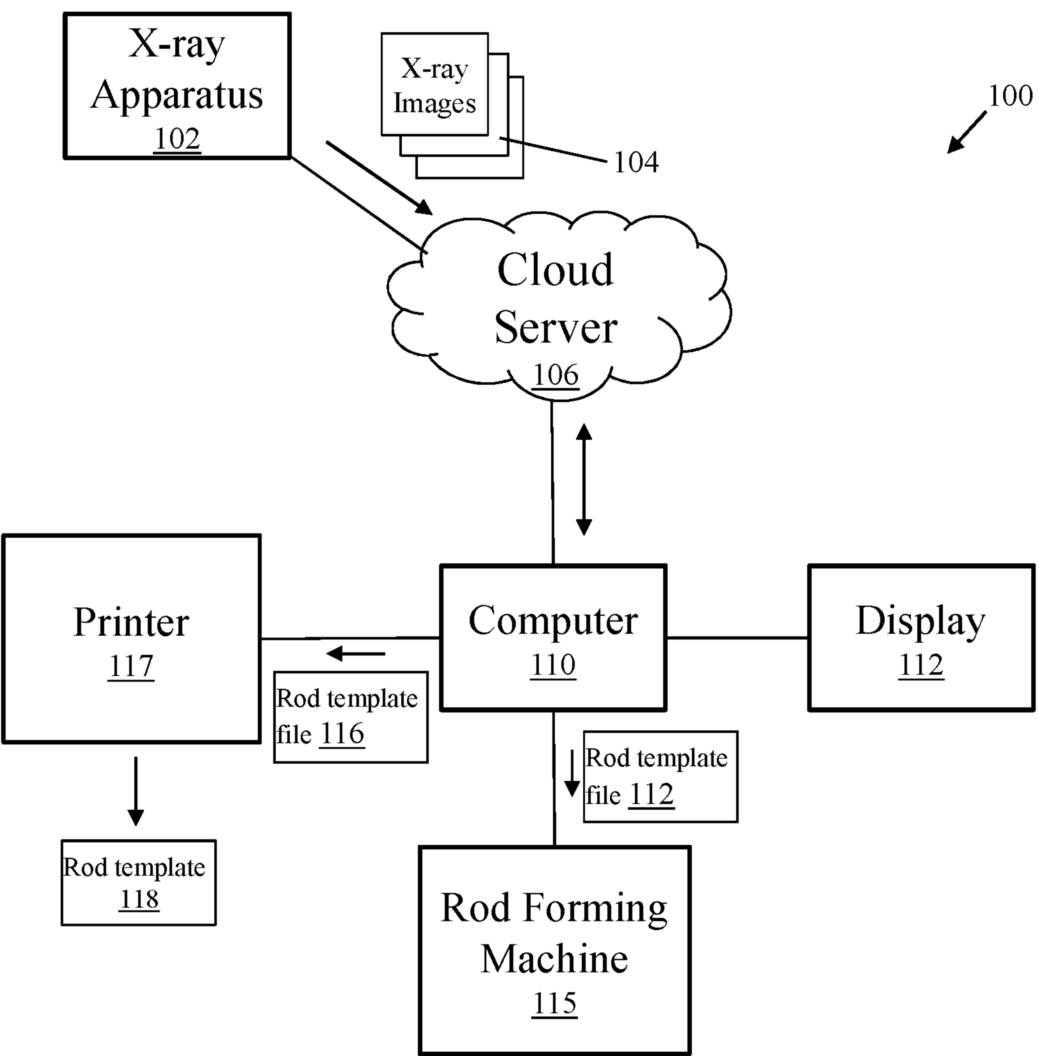
FIG. 1 is a block diagram illustrating a system architecture for developing patient-specific spinal rods in accordance with embodiments of this disclosure.

Embodiments of the systems and methods for developing spinal rods to achieve sagittal balance are now described in detail with reference to the drawings in which like reference numerals designate identical or corresponding elements in each of the several views. As used herein, the term "clinician" refers to a doctor, a nurse, or any other care provider and may include support personnel. In some embodiments, the functions or methods performed by a clinician or surgeon as described herein may be performed, in whole or in part, by a computer or a robot.

Throughout this description, the phrase "in embodiments" and variations on this phrase generally is understood to mean that the particular feature, structure, system, or method being described includes at least one iteration of the disclosed technology. Such phrase should not be read or interpreted to mean that the particular feature, structure, system, or method described is either the best or the only way in which the embodiment can be implemented. Rather, such a phrase should be read to mean an example of a way in which the described technology could be implemented but need not be the only way to do so.

As used herein, the term "sagittal" refers to a plane that divides the body into right and left halves and is parallel to an x-axis, and the term "coronal" refers to a plane that divides the body into front and back (or anterior and posterior, respectively) portions and is parallel to a y-axis.

The goal of some spinal surgeries and the spinal devices that are used in those surgeries, e.g., spinal rods, is to correct a spine so that it is in "balance" with many clinicians focusing on the sagittal plane or "sagittal balance." In short, sagittal balance means that the head is positioned over or aligned with the pelvis from front to back when viewed from the side. Many surgeons use software to guide them through the surgical procedure to ensure that "sagittal balance" is achieved.

In some aspects, this disclosure pertains generally to constructing or forming patient-specific spinal rod templates and implants, and more particularly to using a geometric algorithm, stiffness characteristics, and baseline clinical measures from patient images (e.g., X-rays) to determine a patient-specific spinal rod contour that will generate a predictable post-surgical alignment of the patient's spine when used with a dual differential correction technique.

In some aspects, the dual differential correction method of the present disclosure uses rods of different bends, material, geometry, and order of application to achieve spinal deformity correction. Various data may be used to perform the dual differential correction method. Some of the data may be derived from changes in spinal rod contour from pre-implantation to post-implantation. Other data may be derived from changes in spinal deformity from pre-correction to post-correction. The method may incorporate expected changes in rod shape due to forces of reduction and/or rod application in the treatment of spinal deformities.

In some embodiments, the geometric algorithm may include a process of comparing coordinates of an existing spinal alignment of the patient (also referred to herein as "original spinal alignment") with coordinates of a circle generated to align with a segment of the existing spinal alignment of the patient to allow manipulation of the circle characteristics until an arc portion of the circle is in general alignment with the segment. The geometric algorithm may also process a post-surgical spinal alignment of the patient (also referred to herein as "desired spinal alignment") and generate a second circle with an arc portion of the second circle representative of the post-surgical alignment in view of the existing alignment. In some examples, the geometric algorithm is included in a computer system with a processor and a memory.

In some embodiments, stiffness characteristics may include a shape of the spinal rod. For instance, whether the rod is cylindrically shaped, half-I beam shaped, omega shaped, and so on. In some examples, materials used for the rods may affect stiffness characteristics. Specific stiffness characteristics of the rods may bear a relationship to the loss of contour that may occur due to forces of correction when the rod is applied to a patient's spine at a desired curvature. In some examples, the less of contour in the rod is 20% of the desired alignment. Thus, if a desired kyphosis angle is 16 degrees, then an expected kyphosis angle after performance of surgery may be expected to be approximately 12.8 degrees. The specific loss of contour to be expected in a surgical procedure may vary based on the rod structure itself, as described above, and/or based on the innate characteristics of the patient to be treated, such as the properties of the bone tissue in the spine of the patient. In some embodiments, an over-bend or under-bend algorithm may be executed with a processor of a computer (e.g., FIG. 1) to determine an endpoint post-surgical alignment that accounts for loss of contour.

A general overview of a method according to some aspects of the present disclosure is as follows. In some embodiments, circles placed according to a geometric algorithm in the lateral or frontal images of the spine are used to obtain the best-fit estimation of spinal curvatures. For example, a first circle may be generated that is representative of at least a portion of an existing spinal alignment. Then, a second circle may be generated based on the first circle that is representative of a post-surgical spinal alignment. The circles are used in conjunction with various anatomic landmarks (e.g., posterior vertebral end-plate, posterior vertebral body, posterior sacrum, and/or ribs) to first establish a position of each circle, then, when the circle representative of the post-surgical spinal alignment is generated, to determine the length and shape of a spinal rod template or spinal implant. The use of circles or arcs allows for a rod length determination based on at least one arc segment measurement. The circle that includes the arc may be produced through conversion of angular sagittal spinal column measurements (e.g., thoracic kyphosis or lumbar lordosis). For example, if a thoracic kyphosis angle is known, then radii may be generated based on the angle so that a circumference defined by the radii is aligned with the curvature of the thoracic section of the spine. These relationships may be employed for an existing alignment or for a post-surgical alignment as part of a correction. The method of the present disclosure takes advantage of the relationship between changes in a radius of curvature of the spine and the corresponding implant (e.g., spinal rod) to corresponding changes in angular measurements.

In one aspect, the present disclosure relates to a system for performing a method of determining spinal rod properties. In one embodiment, shown in FIG. 1, a block diagram illustrates an example system architecture for forming a spinal rod. In some embodiments, an X-ray apparatus 102 provides X-ray images 104 to a cloud server 106. Alternatively, images from a modality other than an X-ray may also be provided (e.g., CT scan). The cloud server 106 may be secured in such a way that it complies with the privacy protection provisions of the Health Insurance Portability and Accountability Act of 1996 (HIPAA). In other embodiments, the X-ray apparatus 102 provides X-ray images 104 to a computer 110 or a server that may better protect patient information than cloud server 106. The X-ray apparatus 102 may be any X-ray apparatus that is configured to capture X-ray images 104 of the human skeleton.

The X-ray images may be digital X-ray images, which are typically stored and transferred in a uniform medical format referred to as Digital Imaging and Communications in Medicine (DICOM). The X-ray apparatus 102 may be any suitable digital radiography equipment that is generally calibrated and checked by the manufacturer at the time of installation. However, various digital radiography equipment may fall out of calibration over time. Standardized calibration markers may be added to the image during a process to confirm calibration of the images or allow for use of images in alternative formats including but not limited to JPEG, PNG, and TIFF formats. A standardized radiopaque marker may be worn by the patient at the level of the patient's spine to more accurately calibrate the resultant image. Use of these methods may enhance the accuracy of the resultant calculations for length determination used in constructing spinal rod templates or implants.

Cloud computer server 106 may store the X-ray images in a way to allow for easy access by a computer 110 that has access to the cloud computer or server 106. The computer 110 may then process the X-ray images to determine or generate rod parameters for constructing a spinal rod using a rod forming or bending machine 115 or a three-dimensional printer. In some examples, rod parameters may be generated by the X-ray image itself. In other examples, rod parameters may be generated based on a post-surgical spinal alignment based on the geometric algorithm executed in view of the X-ray image, as described in greater detail elsewhere in the disclosure. Alternatively, the dimensions of the spinal rod contained in a rod template file 116 may be printed using a printer 117, e.g., a digital printer, to produce a mechanical template 118 that can be used by a clinician to manually cut and bend a spinal rod.

Figure 2:
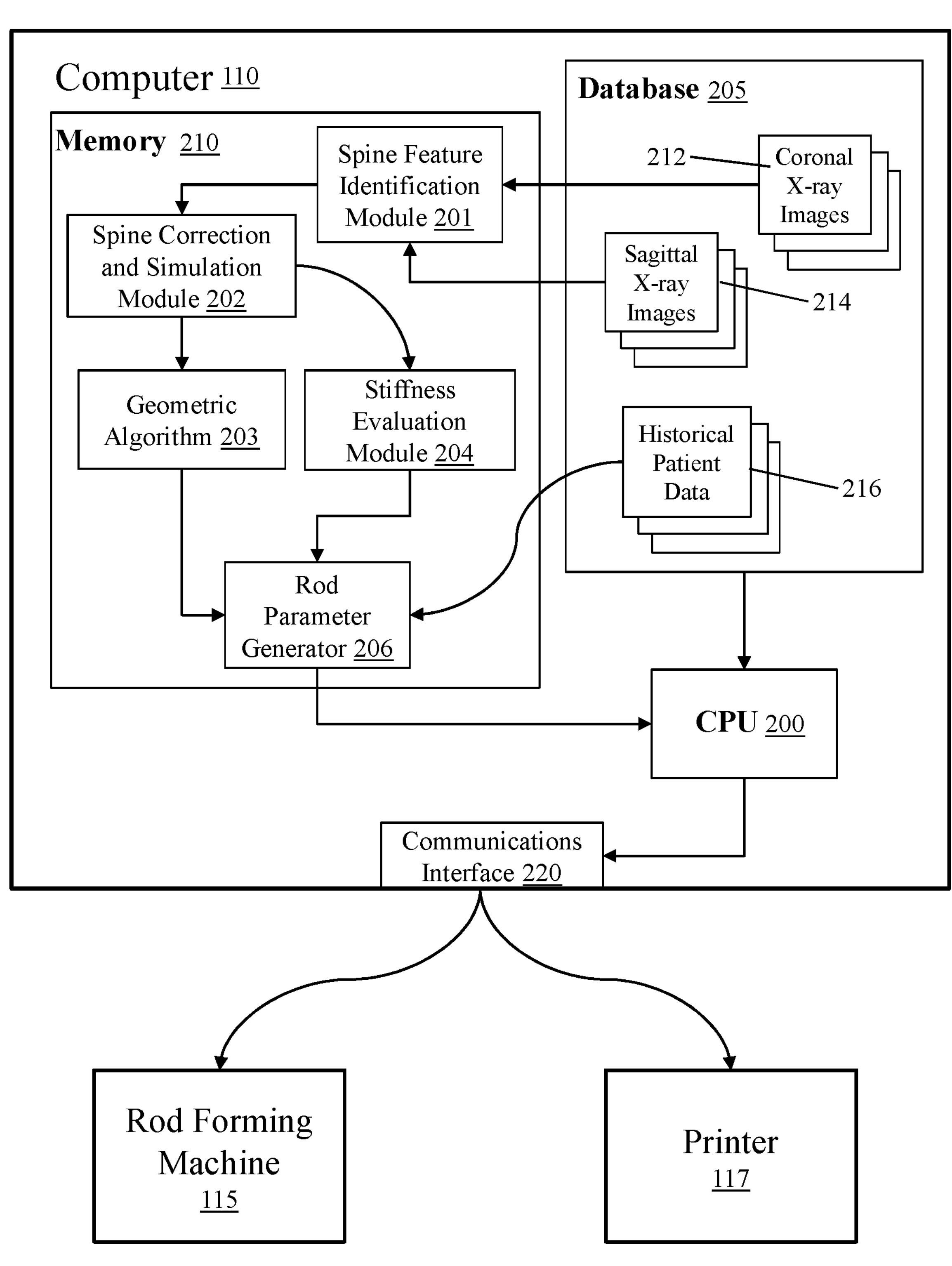
FIG. 2 is a block diagram illustrating a computer system and spinal rod forming machine employed in the system architecture of FIG. 1.

With continuing reference to the system, FIG. 2 is a block diagram illustrating a computer 110 according to some embodiments of the disclosure, which is coupled to the spinal rod forming machine 115 and the printer 117, employed in the system architecture 100 of FIG. 1. Together, the computer 110, rod forming machine 115 and printer 117 constitute a system according to one embodiment of the disclosure. In some embodiments, the spinal rod forming machine 115 may be or may include a three-dimensional printer or a milling machine. Computer 110 includes a central processing unit (CPU) 200, a database 205, and a memory 210. In some embodiments, a portion of the X-ray images stored in the cloud server 106 are retrieved from the cloud server 106 by computer 110 and stored in the database 205. The X-ray images retrieved from cloud server 106 may include coronal X-ray images 212 and sagittal X-ray images 214 of one or more spines. In embodiments, coronal X-ray images 212 and/or sagittal X-ray images 214 are used in the systems and methods of this disclosure.

Computer 110, under the control of the central processing unit 200, may also retrieve historical patient data 216 from the cloud server 106 and store the historical patient data 216 in the database 205. The historical patient data 216 may include pre-implantation and post-implantation spinal rod contour data along with pre-correction and post-correction spinal deformity data from prior surgeries that may be used to predict, for example, cervical lordosis, thoracic kyphosis, or lumbar lordosis if a given spinal rod is applied to a spine of a patient. The historical patient data 216 may be used, at least in part, to determine appropriate parameters (e.g., shape and length) of a spinal rod, or to verify previously determined parameters of the spinal rod. Similarly, such historical patient data may be used in conjunction with or to verify a separate surgical correction plan that utilizes methods of the various embodiments of the present disclosure.

Components of the system of the present disclosure can be embodied as circuitry, programmable circuitry configured to execute applications such as software, communication apparatus applications, or as a combined system of both circuitry and software configured to be executed on programmable circuitry. Embodiments may include a machine-readable medium, e.g., the memory 210 of FIG. 2, storing a set of instructions which cause at least one processor, e.g., the CPU 200 of FIG. 2, to perform the described methods.

Machine-readable medium is generally defined as any storage medium which can be accessed by a machine to retrieve content or data. Examples of machine readable media include but are not limited to magneto-optical discs, read only memory (ROM), random access memory (RAM), erasable programmable read only memories (EPROMs), electronically erasable programmable read only memories (EEPROMs), solid state communication apparatuses (SSDs) or any other machine-readable device which is suitable for storing instructions to be executed by a machine such as a computer.

In one aspect, the present disclosure relates to operation of a computer to perform a method of determining spinal rod properties. In some embodiments, operation of the CPU 200 executes machine-readable code stored in the memory 210. The machine-readable code may include instructions for implementing a variety of software modules including a spine feature identification module 201, a spine correction and simulation module 202, a geometric algorithm 203, a stiffness evaluation module 204, and a rod parameter generator 206. The rod parameter generator 206 receives and processes historical patient data 216, which may be analyzed in conjunction with the outputs from or results of the geometric algorithm 203 and the stiffness evaluation module 204, to produce rod parameters to achieve a desired predicted result, e.g., a desired lumbar lordosis, cervical lordosis, or thoracic kyphosis.

The stiffness evaluation module 204 evaluates the stiffness of the spine to determine the spinal implant material and/or spinal implant geometry. The stiffness evaluation module 204 may evaluate the stiffness of the spine based on one or more X-ray images of the patient's spine in a frontal view with the patient bending to each side, one or more X-ray images of the frontal view of the patient laying supine with traction applied to the extremities, or one or more X-ray images of the frontal view of the patient laying on her side (where the convexity of the deformity is toward the X-ray table) with a bolster placed at the apex of the convexity of the patient's spinal deformity, or any combination of these types of X-ray images. The same stiffness evaluation can be performed on X-ray images obtained in non-weight-bearing patients. However, the weight-bearing X-ray images may be more useful to elicit the effects of the forces of gravity and posture on the shape and position of the spine.

The rod parameter generator 206 generates rod parameters based on the arc length of a circle determined by the geometric algorithm 203. In some embodiments, the rod parameter generator 206 generates rod parameters based on the arc length and at least one of the historical patient data 216 and the stiffness characteristics determined by the stiffness evaluation module 204. The rod parameter generator 206 may additionally generate commands or instructions for controlling the rod forming machine 115, e.g., a milling machine, to form or construct spinal rods according to the parameters generated by the surgical device parameter generator 206. The computer 110 also includes a communications interface 220 that is in communication with the rod forming machine 115 and the printer 117 to provide the rod template files 112, 116 to the rod forming machine 115 and the printer 117, respectively.

Figure 3:
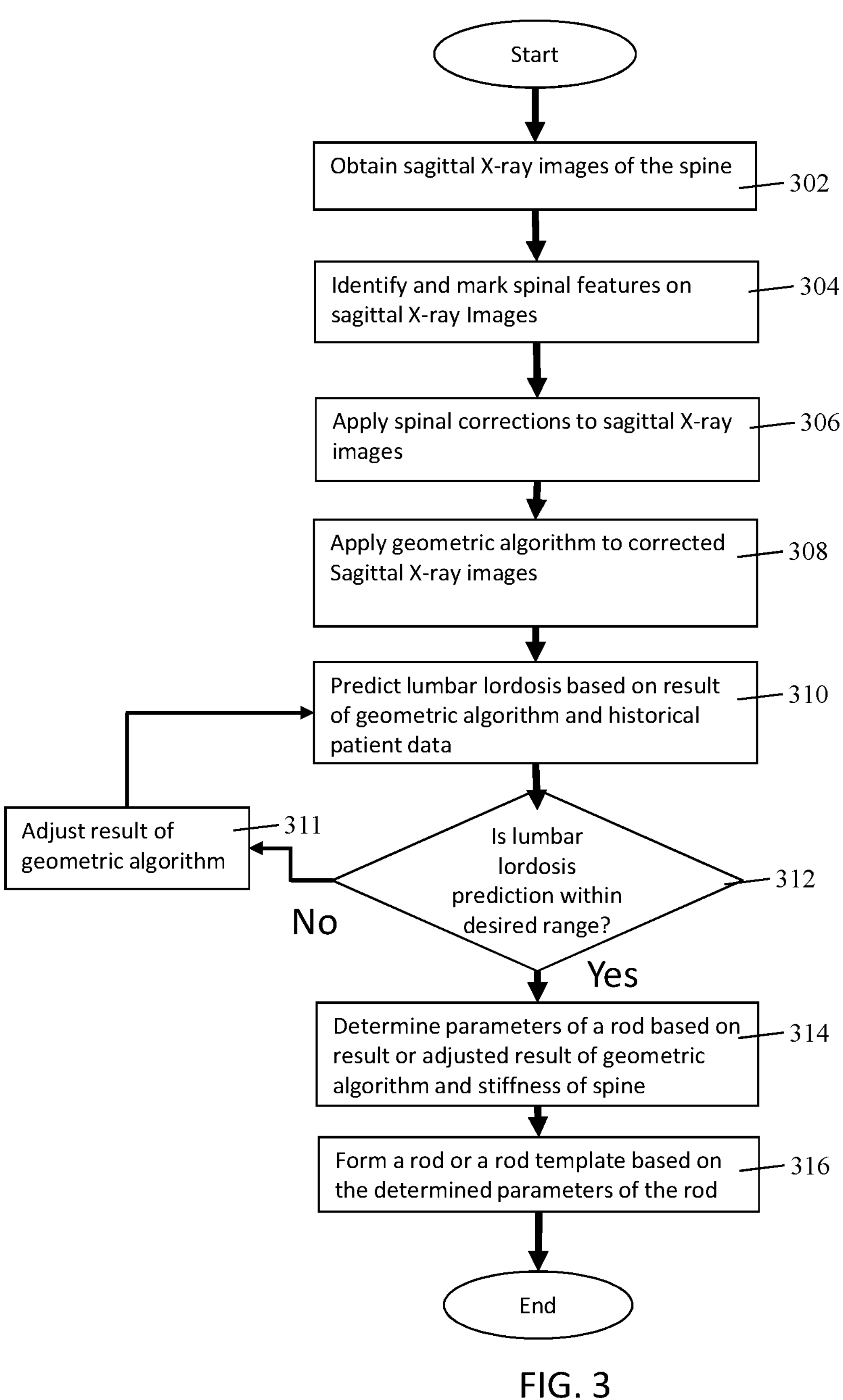
FIG. 3 is a flow diagram illustrating a process for forming a spinal rod in accordance with some embodiments.

In one aspect, the present disclosure relates to a method for performing spinal surgery. FIG. 3 is a flow diagram that illustrates the process for performing spinal surgery in accordance with some embodiments. After starting, sagittal X-ray images are obtained (or images obtained from other modalities) from a cloud computer or other similar database at block 302. In some embodiments, coronal X-ray images are also obtained from a cloud computer or other similar database. The sagittal X-ray images may be X-ray images of a spine and are obtained prior to the surgical procedure. The X-ray images may also include images that were obtained both before and after a previous surgical procedure, e.g., a procedure performed on the spine.

At block 304, relevant spinal features are identified and/or marked on sagittal X-ray images. At block 306, corrections are applied to the sagittal X-ray images to produce a post-surgical spinal alignment inclusive of corrections. At block 308, a geometric algorithm is applied to the corrected sagittal X-ray images to align a portion of a circle, ellipse, or other suitable shape to a portion of the post-surgical spinal alignment shown in the corrected sagittal X-ray images. At block 310, lumbar lordosis is predicted based on the result of the geometric algorithm and historical patient data. Alternatively, lumbar lordosis is predicted based on the circle produced by the geometric algorithm and the stiffness characteristics of the rod. In yet another alternative, lumbar lordosis is predicted based on the circle produced by the geometric algorithm, historical patient data, and the stiffness characteristics of the rod.

At block 312, it is determined whether the prediction is within a desired range. If the prediction of the lumbar lordosis post-surgical spinal alignment is not within the desired range, the result of the geometric algorithm is adjusted, for example, based on an over-bend or under-bend algorithm and/or an analysis of the historical patient data at block 311. In one example, an over-bend algorithm will overcompensate for a first circle representing the post-surgical spinal curvature based on the geometric algorithm, referenced above, by producing a second circle that provides a spinal curvature (including an arc that represents a corrected spinal segment) greater than the first circle generated based on the geometric algorithm with the expectation that, due to historical patient data and/or rod stiffness characteristics, the actual endpoint post-surgical alignment will be within the desired range. In an over-bend application, a radius of the second circle will be less than a radius of the first circle. Similarly, in one example, an under-bend algorithm will produce a circle that defines a post-surgical spinal alignment with a curvature less than that of the alignment predicted by the geometric algorithm alone. If the lumbar lordosis prediction is within the desired range, the parameters of a rod are determined based on the result or adjusted result of the geometric algorithm and the stiffness of the spine at block 314.

At block 316, a spinal rod or a spinal rod template is formed based on the parameters of the rod. For example, the spinal rod may be formed using a milling machine by inserting an object in the milling machine and providing instructions to the milling machine to remove material from the object to form a spinal rod according to the parameters. As another example, the spinal rod may be formed by a machine that receives a spinal rod "blank" and cuts and bends the "blank" according to the rod parameters, which may be in the form of a template. In embodiments, the clinician may use the rod template and appropriate tools, if needed, to cut and bend a spinal rod "blanks" into the spinal rods to be applied to a patient's spine. In some embodiments, the spinal rods are applied by one or more clinicians to the patient's spine according to the dual differential correction method.

Figure 4:
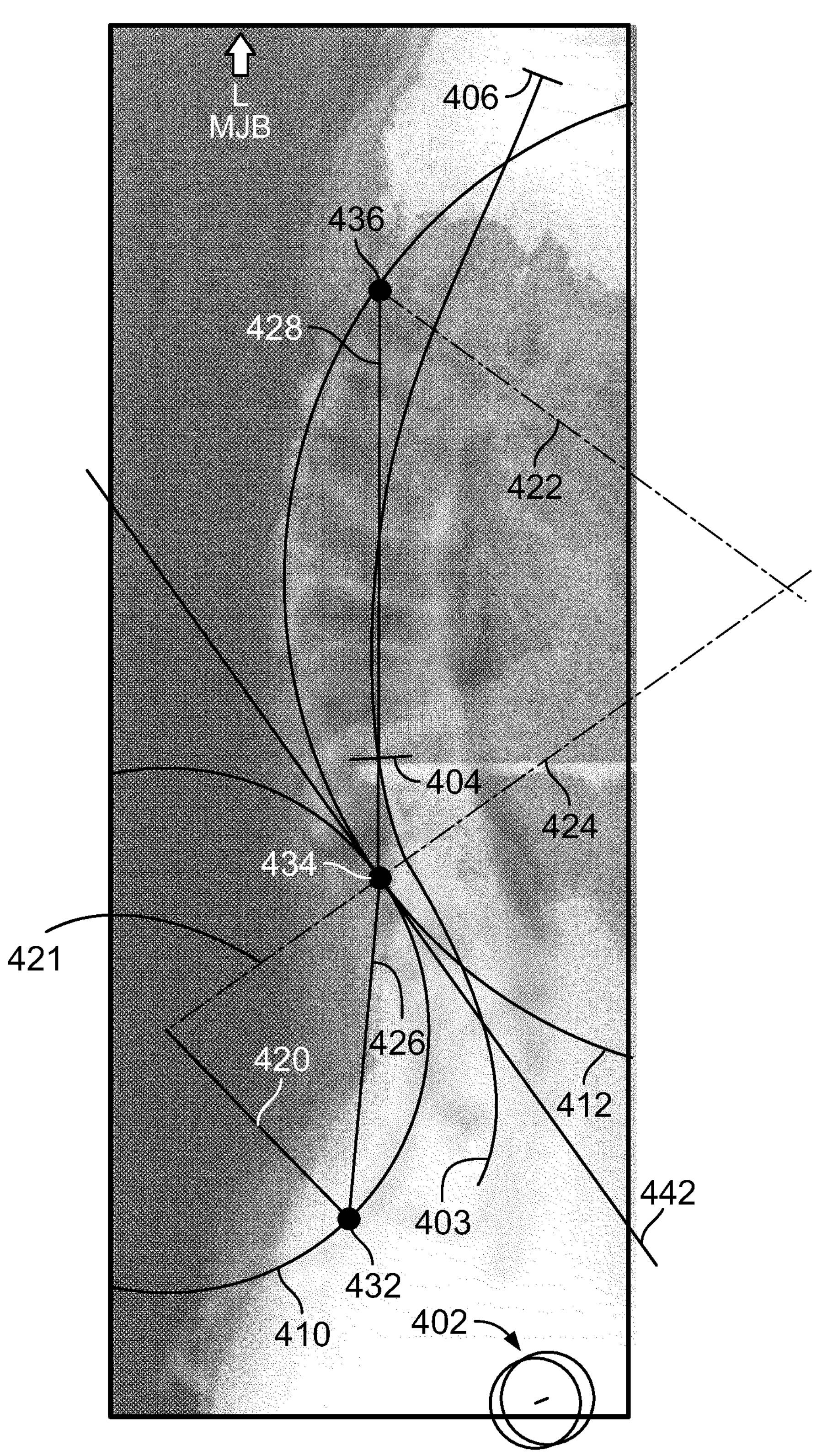
FIG. 4 is an X-ray image of a sagittal view of a preoperative spine illustrating a method for determining parameters of a spinal rod in accordance with some embodiments.

In one aspect, the present disclosure relates to a method of analyzing images of a patient to prepare for a spinal correction procedure. FIG. 4 is an X-ray image of a sagittal view of a preoperative spine illustrating a method for determining parameters of a spinal rod in accordance with some embodiments. In some embodiments, aspects of the method are implemented by one or more software applications, which may be modified Picture Archiving and Communications Systems (PACS) viewers. Examples of the one or more software applications include Surgimap, SpineView, Osirix, Horos, and Keops.

In some embodiments, implementation of the method with a software application includes one or more of the following steps. X-ray images are imported into the software application's database, e.g., the database 205 of FIG. 2, either through a network connection or through portable media such as a portable drive or optical disc. Once the images are recognized by the software application, the spinal measures are completed. In some embodiments, to obtain better alignment analysis, full-spine X-ray images (which may include the head or the base of the skull and extend to the hip joints so that the acetabulum is visible) taken with the patient in a standing position, are obtained. The orientation of the views may include a coronal/frontal view and a lateral (side)/sagittal view.

Anteroposterior (AP) and/or lateral X-ray images may be loaded into a pane (not shown) at the bottom of a database window (not shown) on a graphic user interface (GUI) displayed by a software application. A clinician may select an AP X-ray image (not shown) to load the AP X-ray image into a measurement window (not shown) on the GUI. The image view may be adjusted by the clinician using sliders at the bottom of the X-ray window or the image view may be automatically adjusted according to known methods.

In embodiments, the X-ray image is viewed as if looking at the patient from behind (the patient's left side would be on the left side of the screen). If needed, the clinician may select or click on a horizontal flip button on the X-ray window (not shown). In embodiments, general observations may be made regarding the patient. For example, the number of thoracic and lumbar vertebra are counted so that levels can be recorded appropriately. Shoulder drops, pelvic rotation and/or obliquity may be noted. Any malformations, defects, pedicle size concerns, etc. may also be noted. The clinician may also perform a general evaluation of the bone quality.

The software application may include controls that allow the clinician to zoom in and scroll so that the sacrum and pelvis shown in the X-ray image fill a window. Or the software application, using at least image recognition techniques, may automatically zoom in and scroll so that the sacrum and pelvis shown in the X-ray image fill the window. The software application may further include a tool that drops a plumb line indicating the sagittal vertical axis across the X-ray image and measures a lateral offset. On the X-ray image, the clinician may place the cursor crosshair over the center of the sacrum at its widest point and click on it. In response, the software application drops a line, which represents the central sacral vertical line (CSVL) onto the X-ray image. The software application may display a lateral line that follows the cursor.

The clinician then positions the cursor crosshairs over the C7 spinous process and left-clicks the mouse to measure the coronal offset. The software application may then place the measurement value at the point of the first click. The coronal offset measurement may be positive if the patient's head is to the right of midline and negative if the patient's head is to the left of midline.

Next, vertebrae are identified for level selection:

1. Stable Vertebra: Cephalad vertebra at the bottom of the bottom curve where the CSVL closely bisects between pedicles. The cephalad vertebra do not have to be horizontally level but should not be rotated.
2. Neutral Vertebrae: The lowest neutral vertebra is a vertebra at the bottom of the curve that shows no rotation, e.g., the spinous process is equally between the pedicles and both pedicles are symmetrically visible. There is another at the top of the curve and one between any two curves.
3. Last Touched Vertebra: This is the vertebra that, moving cephalad, is last touched by the CSVL before the spine deviates off midline.
4. Apical Vertebra (e): These are the vertebra or discs that are at the apex of the curve(s) and are most deviated from the midline.

The clinician may zoom out sufficiently so that she can identify the curves. For example, starting with the proximal thoracic curve (if present, the apex falls between T2 and T5), the clinician may click on an angle tool on the GUI to determine Cobb angles of the thoracic curve. Starting on the concave side of the upper most tilted vertebra for the thoracic curve, the clinician highlights and selects an edge of the superior endplate (e.g., endplate 406) on the concave side. Then, the clinician follows the endplate to the opposite side of the vertebra and makes a selection at that location. The clinician repeats this process for the bottom endplate 404 of the bottom vertebra L1 of the same curve. The clinician may start and stop on the same sides of the curve to generate the correct angle measurements. If the Cobb angle (thoracic kyphosis angle) exceeds 100° and the curve is not severe, the clinician probably started the lines from opposite sides of the curve. The clinician repeats this process for the main thoracic and thoracolumbar/lumbar curves (if they are present). The procedure of determining the Cobb angle may be performed for other segments of the spine in a similar manner.

The clinician then identifies the levels of the vertebrae to be instrumented based on her philosophy. The clinician may use the stable vertebra, the neutral vertebra, or the last-touched vertebra for the Lower Instrumented Vertebra (LIV). For the Upper Instrumented Vertebra (UIV) the clinician may choose the neutral vertebra at the upper end of the proximal curve if the curve is structural. A structural curve is a curve that measures at least 25° on a bending or stretch film. Thus, a spinal treatment that employs the securement of rods to the spine will extend over a length approximating a distance between the LIV and the UIV.

The bending or stretch films are used to determine if a curve is structural or compensatory. A compensatory curve is a curve that is originally less than 25° or a curve that bends out to below the 25° cobb angle. The bending or stretch films can also be used to evaluate the flexibility or rigidity of a spinal curve.

To assess the flexibility or rigidity of a spinal curve (also referred to as stiffness of a curve), patients are asked to bend right and left, and AP images of the spine are taken. When a patient with a right thoracic curve (scoliosis, the apex of the curve is offset to the right side when viewed from the rear of the patient) bends to their right, bending into their curve, the curve most often decreases in magnitude. The bending film is compared to the neutral film to determine the difference in magnitude. To accomplish this, the Cobb angle is determined for the bending film as describe above at the same levels and in the same manner as the neutral AP film. For example, a patient may have a 62° right thoracic curve on a neutral or standing AP Scoliosis X-ray image as measured from T5 to L1 (main thoracic curve, right apex at T9). On right bending or stretch films where, for example, the AP X-ray is taken with the patient supine and under traction, that same curve may decrease to a Cobb angle of 37° at the same levels as before. By calculating the percentage change in the magnitude, the clinician and/or a computer running a software application can assess the relative stiffness of the spinal curve.

A flexible curve may be a curve that bends out a large amount from its original magnitude (e.g., 50% or more relative to original curve magnitude). A moderate curve may be a curve that bends out a moderate amount from its original magnitude (e.g., 25-50%). And a stiff curve may be a curve that bends out a small amount from its original magnitude (e.g., less than 25%). The flexibility or stiffness of a curve may then be used to determine the material and geometry of the rod to be used.

The rod material may include, in order of increasing stiffness, commercially pure titanium, titanium alloys, and cobalt-chrome alloys. The commercially pure titanium may include, in order of increasing stiffness, commercially pure titanium of medical grades 2 through 6. The rod geometry may include a circular cross-section or a rail/beam-like cross-section (e.g., a rod having: a rounded section having a substantially circular cross-section, a head portion, and a neck portion that connects and transitions the rounded section to the head portion), which may introduce more stiffness than the circular cross-section. An example of a rod with a rail cross-section is illustrated in U.S. Pat. Nos. 9,295,494, 9,801,662, and 8,814,919, the contents of each of which are hereby incorporated by reference in their entireties.

In some embodiments, a less rigid rod is selected for a spine with a less rigid curved region, while a more rigid rod is selected for a spine with a more rigid curved region. For example, a moderately less rigid rod, such as a pure titanium rod of grade 4 with a circular cross-section, may be chosen for a spine with a moderately less rigid curved region. In another example, a more rigid rod, such as a cobalt-chrome rod with a rail cross-section, may be chosen for a spine with a more rigid curved region.

The lateral or side view (sagittal plane view) is an important view for determining rod bend. It is important to be able to see from the base of the skull to the pelvis, including the hip joints or at least the tops of the hip joints. This allows for the assessment of the overall sagittal balance of the spine and the position of the pelvis.

In some embodiments, identification of points along the spinal anatomy for performance of the method proceeds as follows. Starting at the hip joints, the clinician zooms in and may adjust the brightness or contrast until the femoral heads can be identified. This may be difficult and require the brightness to be lowered. The clinician then selects (e.g., clicks using an input device connected to computer where a system is used) a sagittal alignment tool for drawing a spinal curve on the X-ray image (or image taken with another modality) that aligns with the patient's spine shown in the X-ray image. First, and as shown in FIG. 4, the clinician may identify the femoral heads 402, the sacral endplate 403, the superior L1 endplate 404, the superior T1 endplate 406, and the inferior C2 endplate. In some examples, the width of the endplate marks mirror the anterior-posterior width of the respective vertebra. This ensures the spline bisects the vertebra evenly anterior to posterior. If the estimated sagittal profile does not match the patient's spine, a function in the software may be used to adjust the estimated profile to match the curvature of the spine. For example, a handle feature (e.g., a box) can be added anywhere along the spline by selecting (e.g., double-clicking on) the line of the sagittal profile. The handle then appears on the GUI and can be moved up or down along the length of the spline and can be dragged to the midpoint of the spinal column to adjust the spinal curve. As a result, the software application can generate relevant sagittal measurements based on the spinal curve.

In one aspect, particular approaches may be employed to determine a corrected spinal alignment. In some examples, prior to determining a corrected spinal alignment, the pelvic tilt (PT) may need to be adjustment. If the Pelvic Tilt (PT) of the spine needs to be adjusted as part of a corrective procedure, the entire x-ray can be rotated until the PT is within the desired limits. The software may adjust the measurements accordingly. Sagittal balance indicators (e.g., pelvic incidence (PI)-lumbar lordosis (LL), PT, sagittal vertical axis (SVA), T1 pelvic angle (TPA)) may be initially worsened by this and may indicate that more correction is necessary to balance the patient.

With data for the existing spinal anatomy plotted to coordinates stored for use in the method (e.g., via memory in a computer system), an estimate of a post-surgical spinal alignment is established. In some examples, this may be based on a desired Cobb angle for the thoracic kyphosis and/or the lumbar lordosis. In other examples, a procedure including implants or other corrective prostheses may be simulated to determine the post-surgical spinal alignment. For instance, surgical correction tools can be used to apply intervertebral spacers, osteotomies, and/or column resections to obtain the desired sagittal correction. The additional procedures or implants, when considered, may also be simulated in the software program implemented in the computer system and will provide a simulated corrected spinal alignment as compared to the baseline spinal alignment. The combination of one or more of additional implant (s), procedures (e.g., osteotomies) and rod contours can be used to collectively predict the endpoint post-surgical spinal alignment. The contribution of each member (rod, implant, osteotomy) is collectively reported to determine the endpoint and can be individually applied/unapplied by the software program(s). Use of the software for these applications is described immediately below.

A clinician can construct multiple scenarios by activating or deactivating an applied correction from among a list of possible corrections (e.g., in a data table on a GUI) using an input connected to the computer of the system. The clinician should be realistic regarding the amount of correction that can be achieved with the surgical tools or devices. If there are no limiters programmed into the software used by the clinician to define boundaries on the extent of correction available to the clinician, the clinician can simulate corrections that are not reasonable or even possible to achieve intraoperatively. In some embodiments, limiters may be used to limit the amount of correction to an amount that can reasonably be achieved with available surgical tools or devices. With adjustments to the lumbar spine, the anatomic distribution of lumbar lordosis (lordosis refers to the normal inward lordotic curvature of the lumbar and cervical regions of the human spine) is asymmetric. In some examples, two-thirds of the lordosis may be between L4 and S1.

After obtaining the desired simulated correction, the rod bends can be estimated. The clinician begins by identifying the upper vertebra to be instrumented (UIV) and lower vertebra to be instrumented (LIV). Thus, in one example, the UIV may be T2 and the LIV may be L1. In another example, the UIV may be T2 and the LIV may be S1. Also, the clinician may identify any transition vertebra if the rod will be applied across a junctional region. If the instrumentation is to extend to the pelvis, the approximate level of S2 is estimated (e.g., approximately 25 mm below the base of the S1 pedicle).

In one aspect, the present disclosure relates to methods of determining a spinal rod length based on surgical interventions that utilize spinal rods anchored to a series of vertebral pedicles via pedicle screws. According to one embodiment of the method, a clinician determines a spinal rod length based on a correction of both the thoracic kyphosis curvature in the spine. As an initial condition, the clinician has already obtained image data of the spine which is stored in a computer (e.g., as shown in FIG. 1). The image may be an X-ray image and may be obtained using methods such as those described elsewhere in the present disclosure.

In a first step, a geometric algorithm is performed via the processor in the computer and is used to develop a model based on the existing curvature of the spine. Turning to a lordotic segment of the spine, a clinician uses a circle drawing tool to manipulate a circle creation function (e.g., clicks and drags a circle element on the image of the spine) and generates a circle 410 that either aligns, or generally aligns, to the patient's existing lordosis (i.e., existing spinal alignment). In some examples, the edge of the circle 410 should be tangent to the posterior sacrum and a center of the circle 410 should be level with the L3-4 vertebrae level, which is the anatomic center of lordosis. When the circle 410 is manipulated to best conform to an alignment of the posterior side of the existing spine in the lordotic region, it extends through a first point 432 and a second point 434, both on the spine. In some examples, the line of the circle extends or passes directly through the first and second points. In other examples, the line of the circle passes adjacent to one or both of the first and second points. These examples may apply to any circle described in the present disclosure as possibilities (e.g., circles shown in FIGS. 4, 7 and 9). In one example, first point 432 and second point 434 may be at S2 and L2, respectively. Between these points, an arc segment of the circle 410 is approximately coincident with the spinal alignment, but outside of these points, the remaining arc of the circle 410 curves away from the spine, as shown in FIG. 4. A chord 426 extends between points 432, 434, which may be used to aid in determining a length of the arc segment and by extension information necessary for the establishment of rod size and rod length. Similarly, the radius 420 of the circle 410 may be used to determine the radius of curvature of the arc segment. A tangent of the circle 410 should pass through the posterior superior corner of the upper limits of the lordotic curve-generally near L2.

Turning to a kyphotic segment of the spine, the clinician proceeds to implement the geometric algorithm of the computer in the same manner as described for the lordotic segment of the spine. The clinician manipulates the circle creation function available on the GUI to generate a second circle 412 with a radius 422, 424 that either aligns, or generally aligns, to the patient's existing kyphosis in the thoracic spine. The circle 412 is placed over this section of the spine and, in some examples, if the UIV is in the proximal thoracic spine (T1-4), the circle 412 is overlaid on the spine at the superior, posterior corner of the UIV and at the same time is overlaid on the inferior posterior endplate corner of the LIV (e.g., T12-L2). Thus, when the circle 412 is manipulated to best conform to an alignment of the posterior side of the existing spine in the thoracic region, it extends through a first point 434 and a second point 436, both on the spine. In one example, the first point 434 is overlaid adjacent to or on the inferior posterior endplate corner of the LIV and the second point 436 is overlaid adjacent to or on the superior posterior corner of the UIV. Between these points, an arc segment of the circle 412 is approximately coincident with the spinal alignment, but outside of these points, the remaining arc of the circle 412 curves away from the spine, as shown in FIG. 4. Throughout the disclosure, a part of the circle between the first and second points may also be referred to as a portion. In embodiments with other geometric shapes, such part may also be referred to as a portion of the applicable geometric shape. A chord 428 extends between first point 434 and second point 436, which may be used to aid in determining a length of the arc segment and by extension information necessary for the establishment of rod size and rod length. Similarly, the radius 422, 424 of the circle 412 may be used to determine the radius of curvature of the arc segment.

In the embodiment of FIG. 4, the second point 434 on circle 410 is the same as the first point 434 on circle 412. This geometry is desirable as it renders it simpler to accurately determine a required length for the spinal rod used in the correction procedure. In particular, each circle 410, 412 includes a first tangent 442 that passes between but not through both circles 410, 412, as shown in FIG. 4. In the approach shown in FIG. 4 with alignment evaluated for both the thoracic and lordotic regions, point 434 is also a transition point, representing a transition between a first arc size and shape and a second arc size and shape.

In a second step of the method, the geometric algorithm continues to be employed via the processor of the computer (e.g., computer of FIG. 1) to modify the circle 412 (and/or circle 410) generated in the first step and shown in FIG. 4. The circle is modified to include an arc segment that is in alignment with a post-surgical spinal alignment that represents a corrected post-surgical curvature of the spine. For example, a corrected thoracic kyphosis. It should be appreciated that any combination of the previously generated circles (e.g., 410, 412) may be modified when the method is performed. For example, if it is only kyphosis that requires correction, then circle 412 is modified but not circle 410. If both the kyphosis and the lordosis require correction, then both circles 410, 412 are modified. Again, any combination of modifications to the circles is contemplated based on the surgical correction sought by the clinician. For brevity, the present embodiment will only include a correction of thoracic kyphosis and will refer in part to FIG. 7.

Returning to the method, the clinician manipulates the circle creation function to modify the size and the position of the circle 410. The modification to the circle is made to approximate the desired resultant kyphosis. Thus, to increase kyphosis, the circle is reduced in size and shifted closer to the spine. This creates an increased spinal curvature based on a steeper arc. Additionally, as the circle is modified, the chord 428 is preserved and the points 434, 436 at the ends of the chord 428 continue to contact the circle as it is modified. In this manner, when the first circle 412 is modified to a second circle (not shown) that aligns with a post-surgical spinal alignment for the thoracic kyphosis, the second circle is in contact with points 434, 436. The determination of the post-surgical spinal alignment may include an actual post-surgical spinal alignment sought (i.e., an endpoint post-surgical alignment) that is adjusted to account for loss of contour due to the properties of the spinal rod or the spine itself, as described elsewhere in the present application. Briefly, for example, if the endpoint post-surgical spinal alignment sought to be obtained through correction has a Cobb angle of 20 degrees, then the post-surgical spinal alignment used as a benchmark to establish the second circle may be based on a Cobb angle of 25 degrees to account for an approximately 20% loss in the contour of the spine during and after the procedure.

In an alternative corrective procedure, a similar approach to that described above may be used to reduce the curvature of the thoracic region of the spine. To reduce the curvature, the circle 412 is increased in size and shifted away from the spine, reducing the curvature of the arc (e.g., making it flatter) between the end points of the chord 428. Again, the second circle may represent a post-surgical spinal alignment that does not factor in loss of contour and may be adjusted accordingly so that the actual post-surgical alignment meets surgical expectations. In yet another alternative, if the goal is to maintain the current kyphosis, the size of the circle 412 is adjusted to best approximate the alignment of the patient's posterior vertebral column. In this alternative, again, the two circles should make contact at the desired transition point.

In a third step of the method, the arc length to approximate the rod length is determined. In some examples, the method may be performed, all or in part, by a computer, e.g., computer 110 of FIG. 1. In a first example method, an angle determination tool of a software application is used by a clinician. To illustrate the arc length determination process, the existing original alignment of the spine is used as an example. To obtain a length for use in surgery, the arc lengths generated for the post-surgical alignment should be used (e.g., circle 702 in FIG. 7 or circles 960, 962 in FIG. 9).

Beginning with either circle 410 or circle 412 shown in FIG. 4, the clinician selects each of the circle 410 and the circle 412 and is able to mark a center of each circle based on the data previously stored in the creation of the circles. Because each circle abuts the other at a transition point 434 but the circles do not overlap, the clinician is able to generate a single line extending from a center of circle 410 to a center of circle 412, inclusive of the radius 421, 424 of each circle 410, 412. Then, a separate radius 422 (e.g., to UIV) is marked from the center of circle 412 to point 436 on circle 412 and another radius 420 (e.g., to LIV) is marked from the center of circle 410 to point 432 on circle 410. Data stored in the memory of the computer allows the clinician to retrieve data regarding the generated radius lines and angles therebetween. Thus, the values for radius 420 and angle ¢ between radii 420, 421 for circle 410 are retrievable and similarly, the values for radius 422 and angle ¢ between radii 422, 424 are retrievable. The formula to determine an arc length for each curved segment of the spine is provided below.

$$\text{Arc Length} = \frac{\phi}{360^\circ} 2\pi r$$

In the described embodiment, an arc length is determined based on an arc segment of each circle 410, 412, and the two arc lengths combined define a complete arc length equivalent to a total rod length. As noted above, the principles of this example, though applied to an existing spinal curvature via circles 410, 412, may be similarly applied to circles modified for a desired spinal alignment (see circles 960, 962 in FIG. 9, for example). In such cases, the calculated rod length may represent a length of rod needed for a curvature of the spine after the spinal alignment is corrected. The method is an improvement over methods involving angle measurements taken based on specific vertebral locations in the spine for many reasons. For instance, any irregular alignment of a single vertebra that would otherwise be used to calculate a length of a spine segment is addressed because an entire segment of the spine is considered in the assessment when using circles as described in the embodiments of the present disclosure. Thus, a misaligned vertebra will not affect the result. Further, any changes in curvature along the length of the spine not captured with angle measurements taken at select vertebrae are captured in the methods of the present disclosure because an entire length of the spine is considered, and any number of unique curves within the length may also be considered by increasing or decreasing the total number of circles used to determine an overall spine length.

In one alternative example of the first exemplary method of step three, the determination of arc length, is performed through the use of software such that the clinician may select either the circle 410 or the circle 412 to identify a center of the respective circles. Next, the clinician selects on an icon on a user interface for line creation and then selects respective centers of each circle to create a line that connects the center of one circle with the center of the other circle. Returning to the center of the first circle, the clinician creates a radial line through another selection of the icon and marks a line from the center of thoracic circle 412 to the posterior, superior corner of the UIV. Then, the clinician creates a second radial line through a selection of the icon to mark a line from the center of the lumbar circle 410 to the LIV or the point on the lumbar circle 410 consistent with the S2 level. The point where the two circles meet will be the transition for the rod bend (i.e., transition point) and should be anatomically consistent with the junctional transition. This process is repeated for the alternate circle by applying similar features of the software. The first radial line for each circle should extend to the transition point so that one radial line for each circle meets at the transition point.

Still referring to step three, in a second example method, a chord measurement is used to determine arc length for one or more spinal segments. This is accomplished by drawing a chord from the UIV (e.g., 436) to the transition point 434 for one circle (e.g., one of circles 410, 412) using the software and drawing a second chord from the transition point 434 to the LIV. For each spinal segment represented by the chord, the following equation is used to determine the arc length, which may the actual rod length depending on the planned treatment:

$$\text{Arc Length} = \frac{(\text{chord length}) * \pi * \left(\frac{\phi}{360}\right)}{\sin\left(\frac{\phi}{2}\right)}$$

One advantage of using a chord to determine the arc length is that it allows for an easier transfer of measurements into a drawing software program for constructing a physical template. By using the geometry of arcuate segments aligned with the spine, a more accurate determination of a rod length and rod shape can be obtained when compared to other approaches, such as visualizing an existing spinal curvature and estimating from the existing condition a length of rod required for corrective treatment.

In some embodiments, the second step of the method referenced above also includes modifying the planned post-surgical spinal alignment in light of an expected loss of contour in the spine. One example of a planned adjustment to compensate for loss of contour in the spine is shown in FIG. 7.

Figure 7:
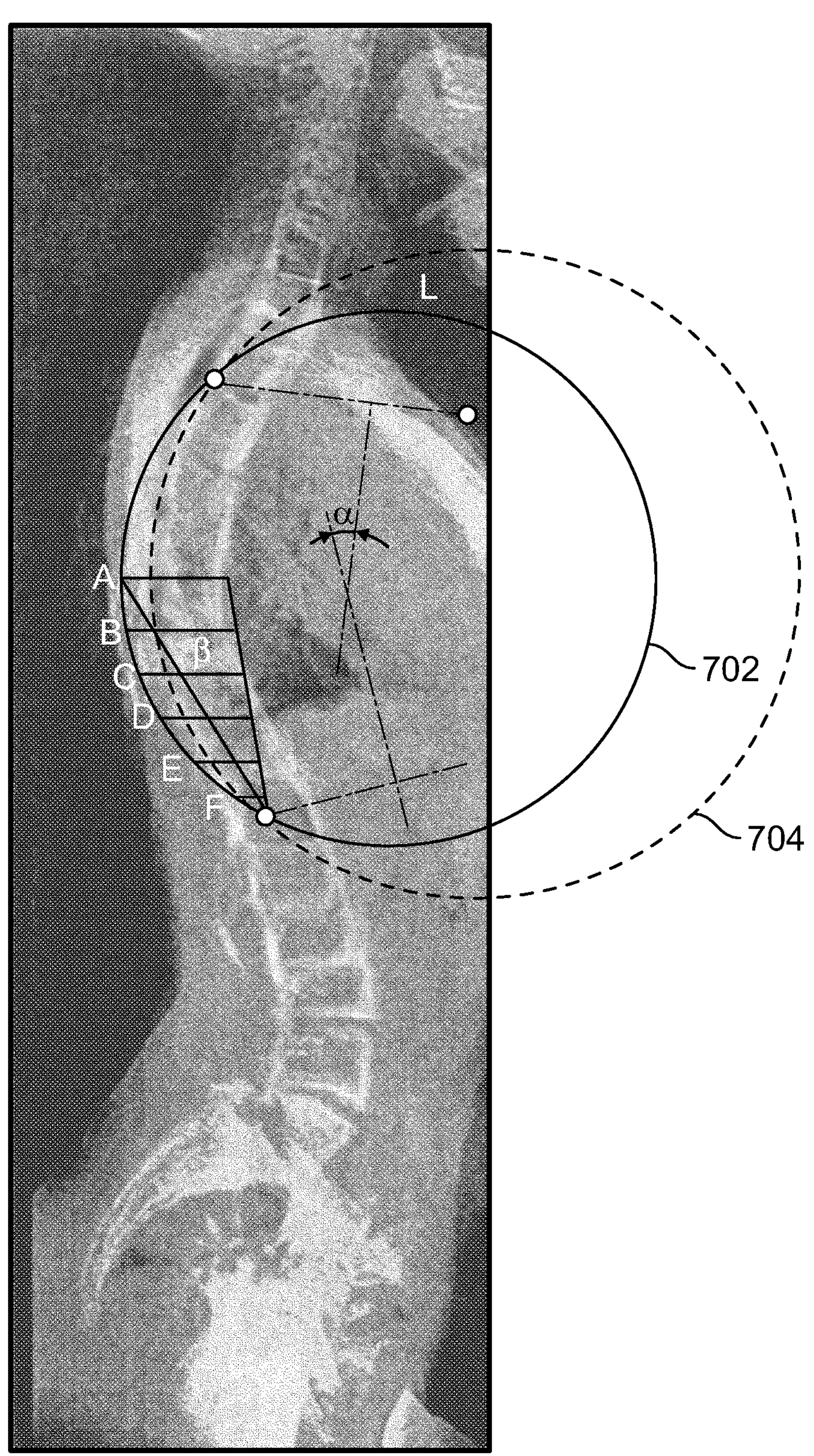
FIG. 7 is a diagram illustrating application of an overbend algorithm to the result of the geometric algorithm in accordance with some embodiments.

FIG. 7 illustrates application of an overbend algorithm to the resulting radii of circles generated according to the geometric algorithm as described above. As illustrated in FIG. 7, a is the original thoracic kyphosis, i.e., original alignment, measured from the superior T4 vertebra to the inferior T12 vertebra (e.g., circle 412 is measured to the original, pre-surgical spinal alignment). β is the estimated additional kyphosis generated from the translation of the spine with the rod as determined by a planned post-surgical spinal alignment based on a radius of curvature of the circle 702 assuming there is no loss in the contour. B is approximately the sum of the angular contributions of each of the individual levels A-F. The circle 702 represents a second circle modified from a first circle (e.g., circle 412) where the second circle represents the post-surgical alignment (the desired spinal alignment) and the first circle represents the existing alignment. In this manner, β is the difference between the thoracic kyphosis at the post-surgical alignment and the pre-surgical thoracic kyphosis, a. Therefore, $\alpha+\beta$ gives the total estimated thoracic kyphosis with surgical correction, i.e., a post-surgical spinal alignment, assuming there is no contour loss. However, it is estimated that at least 20% of the contour may be lost during the correction of the deformity based on observations in three-point bending studies. In practice, greater amounts (e.g., 30-40%) may be observed. As noted elsewhere in the disclosure, loss of contour may occur due to the properties of the rod and/or the bones that constitute the vertebrae. Thus, it should be appreciated that overbend and underbend algorithms are merely examples of how a loss of contour may be accounted for by the computer system or by other means of performing the method. As used herein, references to loss of contour relate to changes in a curvature of a spinal segment. Thus, in one example, a loss of contour may be a flattening of a curvature of an arc or spine.

With continuing reference to FIG. 7, to predict the estimated kyphosis endpoint, i.e., the endpoint post-surgical alignment, for the patient based on the best fit model (i.e., the kyphosis after surgical correction and accounting for loss of contour), the total estimated increase in thoracic kyphosis with surgical correction (β) is added to the result of the angular measurement of the existing thoracic kyphosis (α) described above and the total is multiplied by 0.8 (representing a loss of 20% of curvature), e.g., $0.8\ (\alpha+\beta)$. As illustrated in FIG. 7, the estimated thoracic kyphosis endpoint is represented by circle 704 having a radius of curvature that is approximately 1.2 times the radius of curvature of circle 702, a loss of 20% of the curvature present in circle 702. In this example, the cord distance from T3-T12 remains constant. There will be an increase in cord length with reduction. The arc length or rod length will remain the same. In one example, if an original angle between ends of a spinal segment, for example, an angle between radii 422, 424 in FIG. 4, is 20 degrees, and a planned surgical correction requires that this angle increase to 30 degrees, then the correction should be increased to compensate for an estimated loss of 20% of the curvature. Thus, the planned surgical correction should be based on an angle of 38 degrees. This way, when the spine is corrected to 38 degrees, the endpoint thoracic kyphosis will actually be about 30 degrees (0.8*38° equals approximately) 30°.

With an appreciation for an expected loss of contour, a prediction of a final endpoint thoracic kyphosis post-surgery may be more accurate by allowing a surgical plan to incorporate an estimated loss of contour and therefore include built in extra curvature where the goal is to increase the curvature in the spine. In this manner, a final curvature of the spine may more closely resemble that sought by a clinician based on surgical planning.

Figure 9:
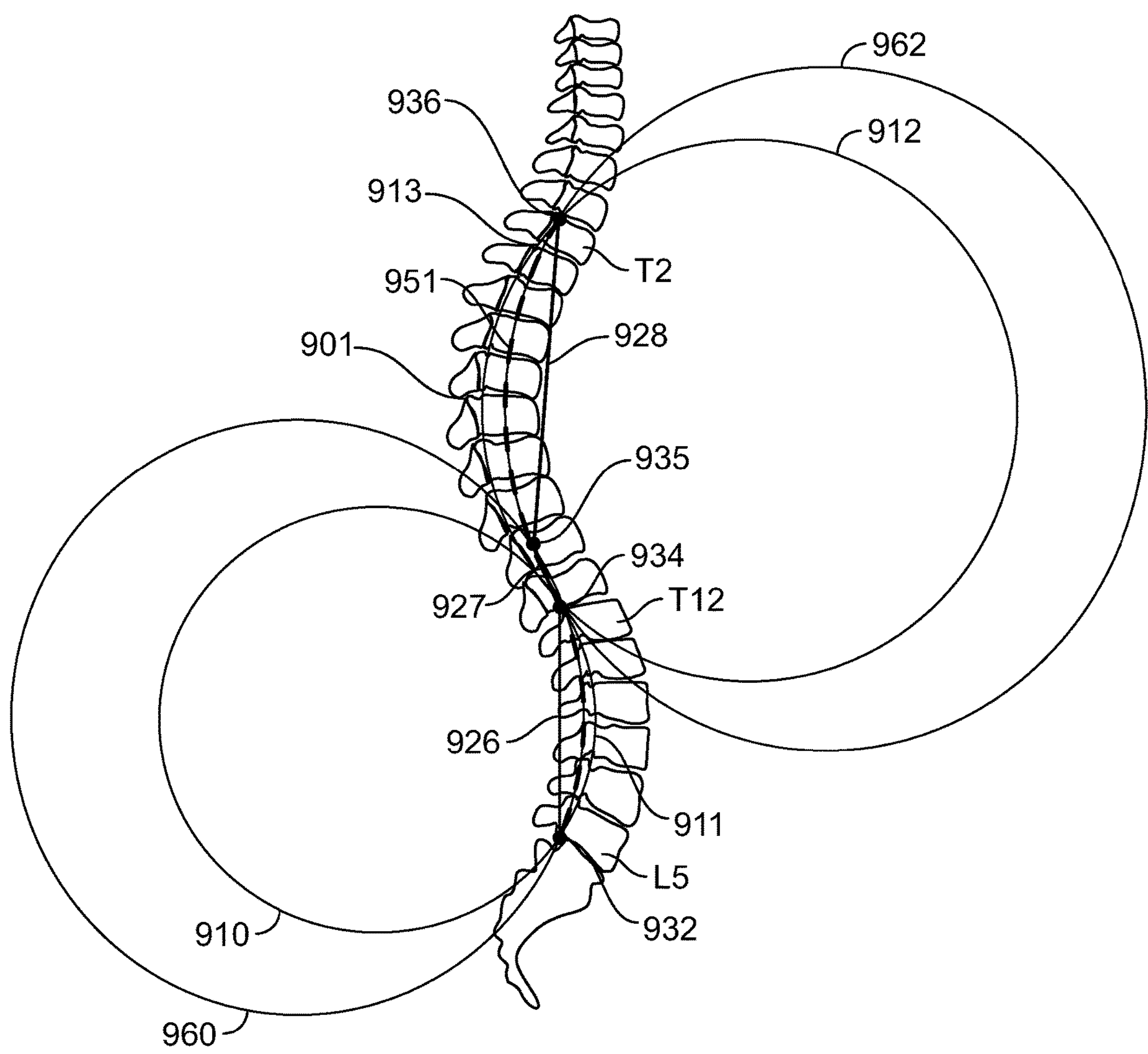
FIG. 9 is a side view of a spine with superimposed circles representing an existing spinal condition and a proposed adjustment.

In another embodiment, a method of correcting the alignment of the spine is shown in FIG. 9. In this instance, the method is performed to reduce both kyphosis and lordosis. Initially, a clinician ensures that sufficient data regarding the existing spine details, including geometry, are stored in the memory of the computer and that such details are scaled for purposes of measurement. Then, the first step through third step are performed with execution of the geometric algorithm on the computer. In some embodiments, as described below, the over-bend or under-bend algorithm may also be executed through the processor of the computer to adjust for loss of contour prior to modify the performance of step two.

In the first step, circles representative of the existing spinal curvature are generated in the manner described for another embodiment above. Here, the first circle 910 and the third circle 912 are generated based on the curvature of spine 901 of the patient, as shown in FIG. 9. In particular, to obtain the first circle 910, the clinician first identifies a UIV and an LIV for the lordotic segment of the spine. These points are located on the posterior side of the spine and as shown in FIG. 9, are located adjacent to T12 and L5, respectively. Based on the curvature of spine 901, the point 934 is also a transition point and an inflection point between a curvature of the lordotic region and a curvature of the thoracic region of the spine. Staying in contact with points 932 and 934, the first circle 910 is generated by shifting and sizing the circle so that an arc 911 of the circle that extends between points 932, 934 is in a best fit alignment with the corresponding thoracic region. A similar approach is used to generate third circle 912 passing through points 934, 936 so that an arc 913 of third circle 912 is in alignment with the spine between the points, while also minimizing any overlap between each circle 910, 912. In an optimal scenario, each circle is generated so that contact between the circles occurs only at point 934.

In step two, and continuing to refer to FIG. 9, each of the first circle 910 and the third circle 912 are modified to capture a desired post-correction spinal alignment. In the depicted embodiment, the desired alignment involves a reduction in curvature of the spine, as shown by a comparison of the existing spinal alignment (spine 901) and the desired alignment 951. In an alternative method, the curvature of the spine may be increased instead using a similar approach. Under these circumstances, each circle must be increased in size to meet the flatter arc required in both the lordotic and thoracic regions as part of the surgical plan. Thus, first circle 910 is modified to second circle 960 and third circle 912 is modified to fourth circle 962. As each circle is increased in size and shifted, the clinician maintains the circle in the lordotic region (first circle becoming second circle) in contact with points 932, 934 in the thoracic region (third circle becoming fourth circle) in contact with points 935, 936. In this manner, once the geometric algorithm is used to modify the circles so that the second circle 960 and fourth circle 962 are generated, the circles 960, 962 generally coincide with the post-surgical spinal alignment.

In the surgical plan shown in FIG. 9, the second and fourth circles 960, 962 cross at two points, point 934 and point 935. A line between points 934, 935 defines a third chord 927. As described in greater detail below, a length of the rod may then be determined based on an arc of circle 960 between points 932 and 934, chord 927 and an arc of circle 962 between points 935 and 936. Through the identification of chord 927, harmony of the rod shape is maintained and a continuous path is provided for the implant.

In another example, the clinician may modify circles 960, 962 further until there is a single point of contact between the circles at point 934 so that the circles 960, 962 do not overlap (not shown). This renders the process of calculating a full arc length combining the lower segment and the upper segment simpler, as described in greater detail elsewhere in the application. As such, the clinician may make further modifications to each circle 960, 962 prior to finalizing the shapes to achieve tangency between the circles. As noted elsewhere in the disclosure, the ability to calculate the arc length for the post-surgical spinal alignment is significant as it may be equated to the spinal rod length.

It should be appreciated that step two as described above does not explicitly account for any loss of contour that may occur when the spinal correction procedure is actually performed. For the desired correction shown in FIG. 9, a loss of contour may occur in the form of a reversion of the flattened arcs to a steeper curve than that provided by alignment 951. In some embodiments, the over-bend algorithm or the under-bend algorithm may be employed to account for the loss of contour. In particular, the post-surgical spinal alignment reflected in circles 960, 962 is modified via an over-bend algorithm to compensate for an expected loss of contour (here, loss of contour would mean the curvature reverting back toward its starting curvature). In practical terms, taking fourth circle 962 for example, the circle is made larger (not shown) to account for a pre-determined percentage loss in contour that is expected to occur when the spinal correction is performed. The larger circle will produce a flatter curve, but because of the loss of contour, the arc of the circle will ultimately match the planned for post-surgical spinal alignment, i.e., the desired curvature. Putting this principle to numbers, if the original cobb angle for the thoracic section of the spine is 20 degrees and the desired final angle with loss of contour is 10 degrees, then, assuming a 20% loss of contour, the planned spinal alignment to be used to account for the loss of contour should be 0.8 ($\alpha+\beta$) where $\alpha=20$ degrees and $\beta=10-20=-10$ degrees. Thus, the planned post-surgical alignment for the surgery would be 8 degrees, and that would result in an endpoint post-surgical alignment with a final angle (endpoint thoracic kyphosis) of 10 degrees. The same principles may be similarly applied to the lordotic region.

In the third step, and continuing to refer to FIG. 9, a length of a spinal rod is calculated using a combination of at least two of the spinal segment angle, radius of circle, and chord lengths to determine a length of one or more arcs that will coincide with the desired post-surgical spinal alignment. The same information may also be used to determine a curvature of the spinal rod. In one example, the rod length is the combined length of arc 911 between points 932, 934 on circle 960, arc 913 between points 934, 935 on circle 962 and chord 927. In another example, the rod length is the combined length of a first arc between points at ends of a thoracic region of the spine and a second arc between points at ends of a lordotic region of the spine, each arc meeting at a single point. In yet another example, the length established may account for loss of contour through consideration of circles that are modified to account for such loss.

The above method embodiments may be varied in many ways. For example, a procedure for the correction of lordosis only may be performed. In other examples, although the methods describe the correction of one or two spinal segments each including the generation of a sequence of circles, the method may also be performed with three or more segments of the spine. Thus, for example, with three curved segments, each may include an initial circle aligned with the segment. One or more of those segments may then be modified to obtain a desired spinal alignment per the method steps as set forth herein. In other examples, the steps of the method may be performed either partially or entirely without any computer executed algorithms.

In still other variations, geometric shapes other than circles may be used. In some examples, elliptical shapes may be used. In some examples, the method may be employed with consideration given to more than a single plane. Thus, while FIGS. 4 and 7 illustrate a corrective alignment in the sagittal plane, in other examples, additional planes may also be considered for the corrective procedure, including the coronal plane and the axial plane. To obtain a corrective alignment based on multiple planes, mathematical equations describing complex shapes can be used to replace the simple geometries and incorporate multiple views (sagittal, coronal and axial) to generate three-dimensional rod contours both for the existing spinal shape and for an optimal spinal shape.

One advantage of the above described method is that by establishing an accurate measure of a length of spinal rod required for spinal correction, the resultant improved alignment in one plane also improves alignment in an orthogonal plane. Thus, if alignment is corrected in the sagittal plane, then the same correction will also correct the alignment in the coronal plane. This three-dimensional correction is made possible by the improved performance of the rods and other implant components through the methods described herein. Another advantage is that curvature of the spine above T4 may be considered when executing a surgical plan. For example, a UIV can be located at T1 and measurements may be determined from that level.

In another aspect, the method may also involve a step of adjusting an expected curvature in one segment of the spine based on a planned correction in another segment. A goal of this consideration is to confirm that the estimated kyphotic endpoint provides a result consistent with sagittal balance health-related quality of life (HRQOL) measures. To accomplish this result, a suitable equation based on a sagittal alignment norm may be used. The equation is useful to verify that a planned spinal correction in one spinal segment, such as the thoracic region, does not adversely affect the curvature in the lumbar region. In some embodiments, the suitable equation may be based on the historical patient data 216 stored in the database of FIG. 2. In some embodiments, empirical equations may be used based on specific pathologies and whether the patient is an adolescent or an adult. For Adolescent Idiopathic Scoliosis (AIS), the following equation may be used:

$$\text{Predicted LL}=0.3187\ \text{TK}-0.3502\ \text{PI}-0.1667\ \text{S1 overhang}+1.274\ \text{SS}+0.5821\ \text{PT}+9.063,$$

For Adults, the following equation may be used:

$$\text{Predicted LL}=-9.13847+0.19225\ \text{TK}+1.54225\ \text{SS}-0.26799\ \text{PI}+1.39705\ \text{T9 tilt}$$

It should be appreciated that the above empirical equations are derived from subsets of patient populations and other empirical equations may be used that represent different subsets of patients with different pathologies.

Figure 10:
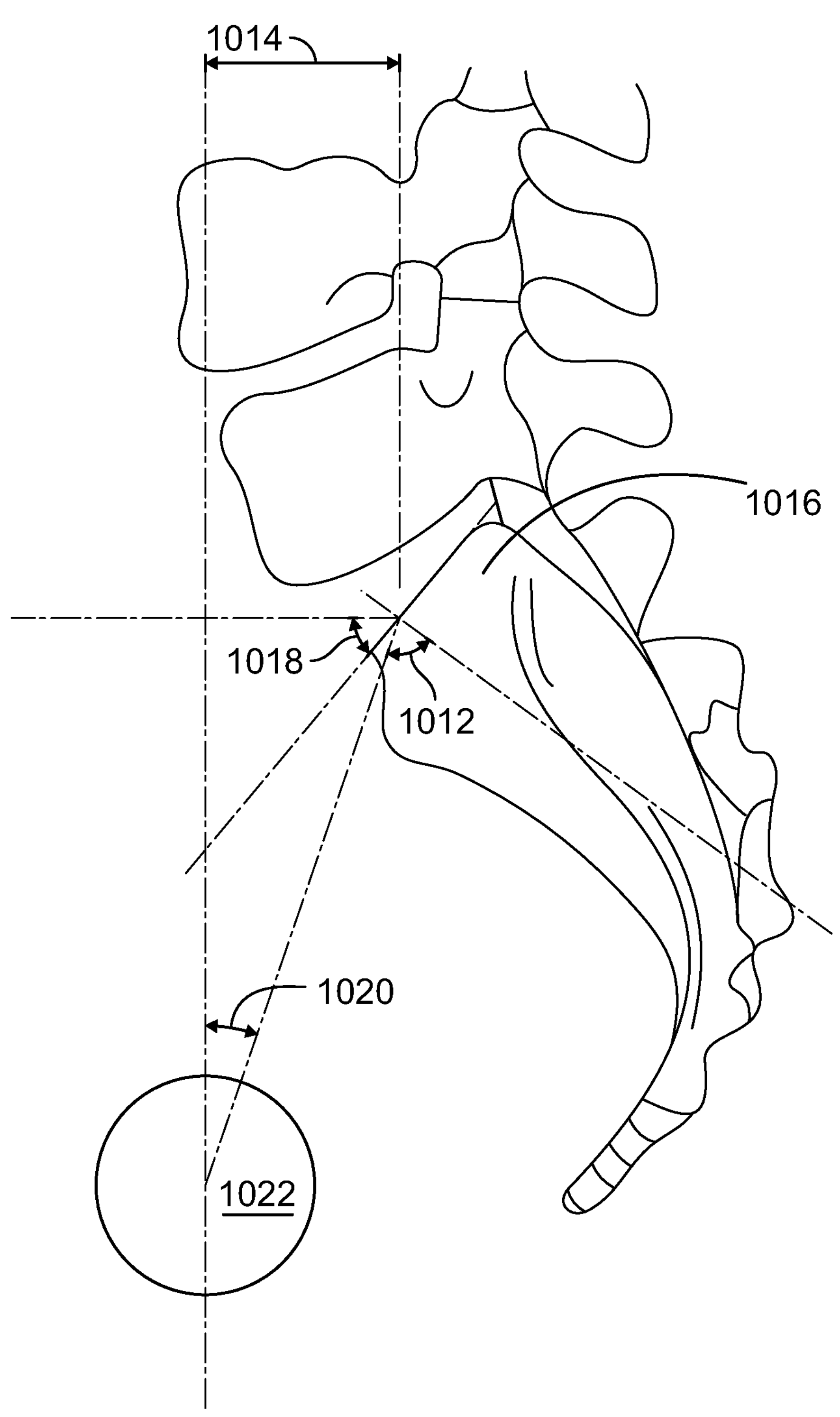
FIG. 10 is a close up side view that shows various measures at the base of the spine.

As shown in FIG. 10, pelvic incidence (PI) 1012 is the angle between the line perpendicular to the sacral plate at its midpoint and the line connecting this point to the femoral heads axis centered on femoral head 1022. S1 overhang 1014 is the geometrical range between the middle of the upper plate of the first sacral vertebra (S1) 1016 and the bi-coxo-femoral axis. Sacral slope (SS) 1018 is the angle between the sacral plate and a horizontal line. Pelvic tilt (PT) 1020 is defined by (1) the line through midpoint of the sacral plate and midpoint of the femoral heads axis, and (2) the vertical. T9 tilt (not shown) is the angle between the lines linking the midpoint of the femoral heads axis with the center of the T9 vertebra body, and the vertical crossing the midpoint of the femoral heads axis. TK is a thoracic kyphosis based on an endpoint post-surgical spinal alignment, and LL is a predicted post-surgical lumbar lordosis (full angle). In some embodiments, TK and/or LL may incorporate loss of contour.

For each equation, the measurements may be obtained from a sagittal alignment tool, e.g., the sagittal alignment tool of Surgimap. To utilize the equations, measurements are plugged into the appropriate variables of the equations (e.g., PI, S1 Overhang, SS, PT, PI, and T9 tilt). In some examples, the endpoint post-surgical thoracic kyphosis (corrected spinal alignment) is obtained as described elsewhere in the disclosure (e.g., from the angular measurements of the circles resulting from the geometric algorithm described above). The TK data, combined with measurements for the other inputs, may be used to determine a corresponding predicted LL. In one example, using this technique for AIS patients, a change of TK by 5° may result in an increase of PT of 2° and a corresponding decrease of SS by the same amount based on the equation. In another example, an increase in TK may result in an increased in predicted LL. In some embodiments, when the predicted LL is known, the predicted LL should meet the following criteria to correspond with an accepted range:

$$PI-LL<\pm 9^\circ$$

If the predicted TK generates a predicted LL outside of this range, the size of the circle is adjusted along with the corresponding measurements to determine an appropriately sized circle and hence, the radius of curvature for the spinal rod. These changes may also be incorporated into the predicted LL equation to determine the predicted LL. To apply these predictive equations to the methods described elsewhere in the application, such as the method illustrated in FIG. 9, a clinician may compute a predicted LL after determining a predicted TK based on the correction method using circles. Then, the desired post-surgical alignment in the lordotic region may be modified in view of the predicted LL and, in some cases, based on loss of contour. The aforementioned equations are advantageous in that they provide an identified spinal alignment to use in conjunction with the others described in the present disclosure to best determine a length or shape of a spinal rod.

Figure 5:
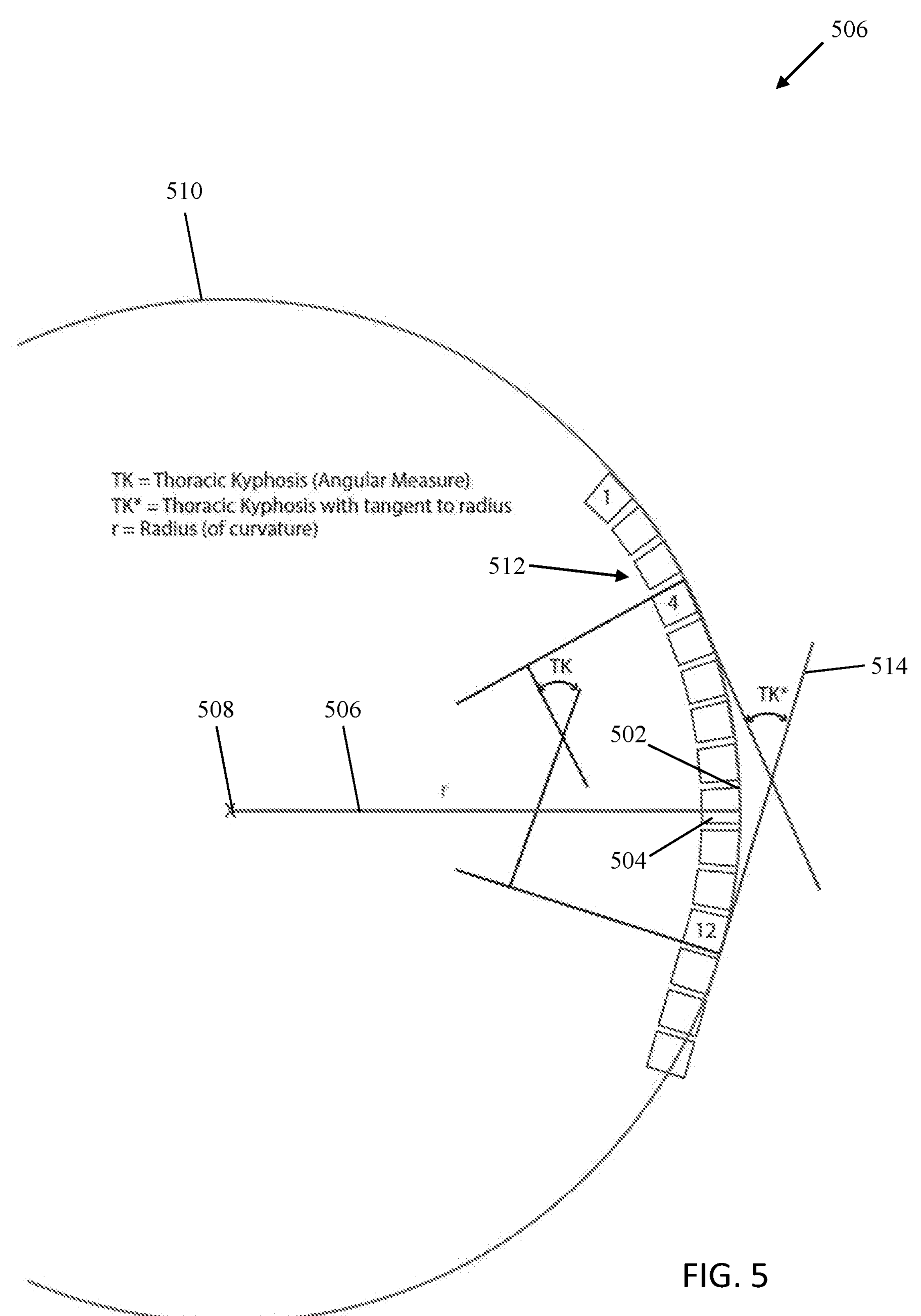
FIGS. 5 and 6 are diagrams illustrating geometric methods or algorithms for determining angular measurements for thoracic kyphosis and lumbar lordosis in accordance with some embodiments.
Figure 6:
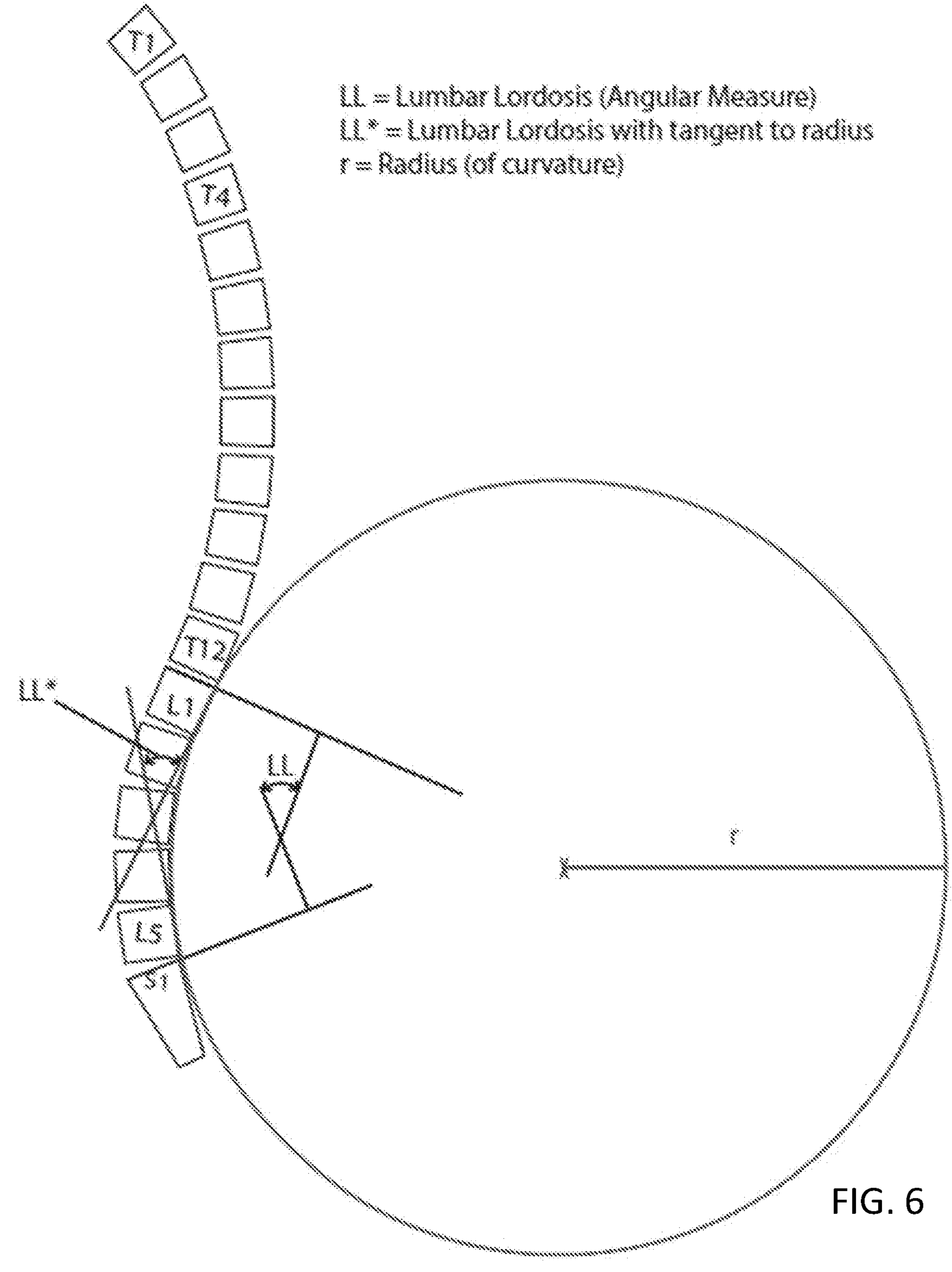

In some embodiments, an alternative manner of determining a thoracic kyphosis and a lumbar lordosis in an existing spinal alignment is employed as shown in FIGS. 5 and 6. As illustrated in FIG. 5, and as similarly illustrated in FIG. 6 for lumbar lordosis, a clinician uses an angle formation input tool to provide instructions to the computer. The clinician selects the posterior, superior corner 502 of the apical vertebra 504. The apical vertebra 504 is determined by following a horizontal line 506 from the center 508 of the circle 510 to the vertebral column 512. In some embodiments, the horizontal line 506 may be drawn from a center 508 of the circle 510 with a line tool, if desired. Next, the clinician clicks to start the angle measure at the apical vertebra 504 and extends a chord 514 tangent to the circle 510 at the LIV at T12. Next, the clinician returns to the level of the center of the circle and clicks again to start the second part of the angle. This time, the clinician selects the point on the circle at UIV, here, at T4, and generates a line tangential to the circle 510 at UIV. With these measures, thoracic kyphosis TK may be measured based on end plates (T4, T12) of vertebrae and thoracic kyphosis TK* may be measured based on an angle between tangents of circle 510 measured at the same end plates. An illustration of these measurements is shown in FIG. 5. If TK is not equal to TK*, the radius of circle 510 may be adjusted until TK equals TK*. In an alternative approach, circle 510 may be sized and positioned to contact a maximum number of points along the posterior vertebral column and provide a direct radial measurement that better represents the curvature of the spine than an angular measure which represents the angle between the two end plates. Similar principles may be employed in the lordotic region, as shown in FIG. 6. In some embodiments, all or a portion of the geometric algorithm or method may be performed by a suitable computer system, such as the computer 100 of FIG. 1.

Figure 8:
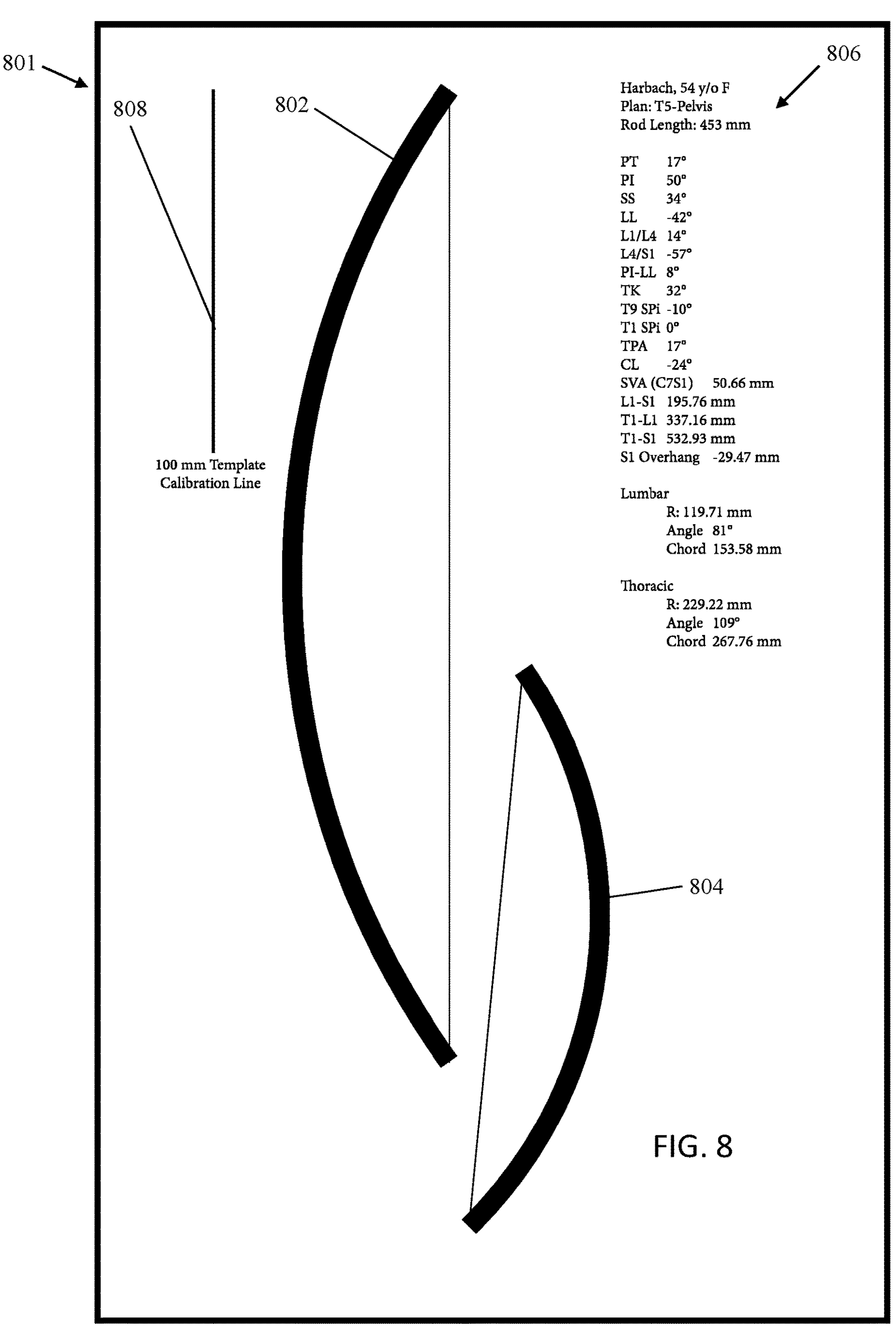
FIG. 8 is a diagram illustrating an example template used to form a patient-specific spinal rod in accordance with some embodiments.

In another aspect, the present disclosure relates to a method of constructing a template. In one embodiment, as illustrated in FIG. 8, a template 801 may be constructed one-to-one using a commercially available drawing program, e.g., Adobe Illustrator. A drawing program provides verifiable accuracy for generating the actual templates used to form (e.g., cut and bend) the spinal rods. The template 801 includes measurements 806, such as the measurements for the circles, chords, and arcs, and template spinal rods 802 and 804, which are constructed in the drawing program based on the measurements 806. The template 801 may also include a template calibration line 808 of known dimension for calibrating the final printed template. For example, as illustrated in FIG. 8, the template calibration line 808 may be 100 mm in length and 1 mm in width. The template 801 may be printed or provided to a machine, which may automatically form appropriate spinal rods for a patient based on the template 801. In embodiments, the spinal rods are prepared ahead of surgery so that valuable time is saved in the operating room.

In yet another aspect, the dual differential correction technique or method used to form spinal rods as described elsewhere in the present disclosure may be employed to attach the spinal rod(s) to the patient's spine. In one embodiment, this technique uses two rods having appropriate bends, material, and geometry, and applies the rods in a particular order, to achieve spinal deformity correction. According to the technique, when using two rods, the convex rod is first applied to the patient's spine, then the concave rod is applied to the patient's spine. After the rods are applied, they are locked down. In other words, the convex and concave rods are not locked down until after they are both applied to the patient's spine. In other embodiments, the method of attaching the spinal rods may be employed for any number of rods having any designated curvature.

In one aspect, the present disclosure relates to a method of performing a dual differential correction technique. The following is a detailed description of an example dual differential correction technique that may be employed to apply rods, which are formed using the systems and/or methods of the present disclosure, to a patient's spine. The general philosophy for treating a lumbar primary or structural curve does not differ from treating a main thoracic curve in that the order of correction proceeds in the same fashion. According to the dual differential correction technique, the choice of the rod is switched between the concave rod and the convex rod, and the direction of correction is reversed (distal to proximal). The order of forces, however, remains the same—the dual differential technique will first push on the convexity of the curve and then will pull.

For many patients, including patients with a left lumbar curve with or without a right thoracic curve (e.g., patients with Lenke 3, 4, 5, and 6 curves, or patients with adult curves), the more rigid/contoured rod is placed on the patient's left side. This allows a push on the lumbar convexity and a pull on the thoracic concavity. The more flexible/less-contoured rod is placed on the patient's right side. This allows for a pull on the concavity of the lumbar spine and a push on the convexity of the thoracic spine. For example, a Ø5.5 mm Ti6Al4V alloy rod (Gold) may be chosen for the patient's right side.

When treating a lumbar primary/major curve (Lenke 5 or 6) or treating a double/triple-curve (Lenke 3 or 4), the left/more rigid/more contoured rod is placed first starting distal and proceeding proximal. According to the dual differential correction technique, the surgeon starts by placing deformity reduction jacks (DRJs) on the most distal 2-3 levels on the convex side of the curve. In embodiments, the surgeon gives the DRJs one turn to apply them but does not close the reduction too much. The surgeon inserts the left-side rod, e.g., a rail, so that ~5 mm of the left-side rod extends distal to the outer collet of the most distal screw. The rail is a rod having an elongate rounded section having a substantially circular cross-section, an elongate head portion, and a neck portion that connects and transitions the elongate rounded section to the elongate head portion. Examples of the rail and associated components are described in U.S. Pat. Nos. 9,295,494; 9,801,662; and 8,814,919, the contents of each of which are hereby incorporated by reference in their entireties.

The surgeon orients the rod into the correct alignment for the sagittal plane and fully tightens the distal-most DRJ. The surgeon brings the other two DRJs down until they "kiss" the rod. Proceeding proximally, the surgeon applies DRJs to the remaining screws. One person may grab the proximal end of the rod with either the rod wrench or a ratcheting gripper. The surgeon steers the rod over the next screw to make it easier for applying the DRJ. The surgeon is again careful not to reduce the DRJs during application—the surgeon gives the DRJ enough of a turn to apply the DRJ securely to the screw but not to reduce the throw of the anvil on the DRJ (e.g., about 1 1/12 turns). This allows the surgeon more mobility and less struggle to place the remaining DRJs.

The surgeon completes the application of all DRJs before beginning any reduction. Once all DRJs are applied, the surgeon starts reducing the DRJs from distal to proximal. The surgeon does not reduce the DRJ beyond the point where the knurled top of the DRJ begins to enter the housing of the DRJ (this keeps the rod/rail from being introduced into the inner collet of the screw). The surgeon reduces all the DRJs in similar fashion up to the transition level (or the proximal end of a Lenke 5 curve).

Next, the surgeon applies the right-side rod (e.g., a titanium alloy rod) in a similar fashion. The surgeon places the first 2-3 DRJs on the distal most levels. The surgeon inserts the rod through the DRJs leaving, for example, Ø5.5 mm of the rod extending beyond the lowest screw. The surgeon adjusts the rod into the appropriate sagittal plane orientation and tightens the distal screw. The surgeon proceeds in a similar fashion so that the next two DRJs are advanced to "kiss" the rod. The surgeon applies the remaining DRJs in the same fashion to the proximal end of the rod.

Once all the right-side DRJs are placed, the surgeon reduces the DRJ at the transition level. The surgeon may reduce the DRJ fully to leave it tight or, if the surgeon wants to allow for some travel, the surgeon may reduce the DRJ fully and then back off half a turn. The surgeon alternates between the distal screws and the transition level, gradually working towards the apex of the lumbar curve. Gradually, the surgeon reduces the DRJs proceeding back and forth as not to point-load any one screw. The rod will slowly bend more as the reduction proceeds and will de-rotate the lumbar spine in the process. Once the DRJs on the right side are all fully reduced, the surgeon completes any compression distraction for the lumbar curve and any in Situ bending that may be desired. The surgeon then corrects the lumbar curve to satisfaction. The surgeon may square or level the transition level to the first free lumbar level to balance the coronal position. The surgeon reduces the left-side lumbar DRJs up to the transition level.

If necessary, the surgeon treats the main thoracic curve in the usual fashion of a simple right thoracic curve—the surgeon starts proximal on the convexity. The surgeon may look at the rod length proximally and make sure it is appropriate before the surgeon locks down the proximal level. The surgeon reduces the remaining DRJs proximal to the transition level applying the cantilever push stopping the advance of the DRJ before the knurled portion enters the housing. Next, the surgeon reduces the left-side DRJs alternating top to transition level working outside-in towards the apex of the thoracic curve. Once all the left-side thoracic DRJs are reduced, the surgeon completes any compression or distraction and in Situ bending that is desired. Then, the surgeon reduces the right-side thoracic DRJs. If the desired correction is complete, the surgeon locks over the DRJs and removes them and then finally locks the DRJs if necessary (e.g., if using the Partial-lock over-the-DRJ locker).

In one aspect, the present disclosure relates to a method of manufacturing a spinal rod. In some embodiments, the method commences with the capture of an image(s) of the spine in an existing condition. The image(s) may be taken with an X-ray, for example. Then, using information from the image(s), a segment or segments of the spine are identified for correction. In some examples, this may be a thoracic region, a lordotic region, both, or other segments of the spine. When the relevant segments are identified, a method of determining a length of spinal rod to be used in the correction of the spinal alignment is performed, as described in other aspects of the present disclosure. Once the length of the spinal rod is determined based on one or more arc lengths, the spinal rod is formed with the required length using a milling machine or cutting a blank using a template, as described in the present disclosure. The curvature of the rod may also be used to form the spinal rod so that it is formed with a curvature in accordance with the one or more arcs representing an endpoint spinal curvature.

In one aspect, the present disclosure relates to a spinal rod structure. In some embodiments, the spinal rod structure includes a body with a length determined based on a method of determining a spinal rod length as described in other aspects of the present disclosure. In some examples, the cross-sectional shape of the rod is circular while in others it may be a half-I section, omega shaped, T-shaped or other shapes used in spinal correction surgery.

While several embodiments of the disclosure have been shown in the drawings, it is not intended that the disclosure be limited thereto, as it is intended that the disclosure be as broad in scope as the art will allow and that the specification be read likewise. For example, although this disclosure describes the application of the geometric algorithm to sagittal X-ray images, the geometric algorithm may also be applied to coronal X-ray images, to a combination of sagittal and coronal X-ray images, or to images obtained through other modalities. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

The invention claimed is:

1. A method of planning for spinal correction surgery using a system having a processor and a memory and a rod forming machine, the method comprising:

storing a pre-operative image of a spine of a patient in the memory of the system;

identifying a segment of the spine requiring correction using the pre-operative image of the spine stored in the memory, the segment including a first point along the spine at a first end of the segment and a second point along the spine at a second end of the segment;

determining a first radius and a first position of a first circle based on the pre-operative image by using the processor such that a portion of the first circle is generally aligned with a curve of the segment and the first circle passes adjacent to or through the first point and the second point;

based on a planned post-surgical spinal alignment, modifying the first circle to define a second circle by using the processor, the second circle having a second radius and a second position based on the pre-operative image such that the second circle passes adjacent to or through the first point and the second point, a portion of the second circle from the first point to the second point representing the planned post-surgical alignment of the segment, wherein the second radius is different from the first radius;

measuring, by the processor, an arc length of the portion of the second circle; and forming a rod using the rod forming machine so that an elongate dimension of the rod is based at least in part on the arc length of the portion of the second circle, the rod being curved prior to being implanted into the patient, and the rod being configured for use in conjunction with pedicle screws to correct the spine.

2. The method of claim 1, further comprising:

identifying a second segment of the spine requiring correction including a third point along the spine at a first end of the second segment and a fourth point along the spine at a second end of the second segment;

establishing a third circle based on the pre-operative image using the processor such that a portion of the third circle coincides with a curve of the second segment and the third circle passes adjacent to or through the third point and the fourth point, the third circle having a third radius and a third position on the pre-operative image; and modifying the third circle to define a fourth circle by using the processor, the fourth circle having a fourth radius and a fourth position on the pre-operative image such that the modified third circle passes adjacent to or through the third point and the fourth point.

3. The method of claim 2, wherein one of the first point and the second point is the same as one of the third point and the fourth point.

4. The method of claim 2, wherein prior to modifying the third circle, the first circle and the third circle share a common tangent.

5. The method of claim 2, further comprising modifying one of the second circle and the fourth circle so that each of the respective circles, as modified, share a common tangent.

6. The method of claim 2, wherein the third point is located at vertebra T12, L1 or L2 and the fourth point is located at vertebra L5, S1 or S2.

7. The method of claim 1, wherein a dimension of the first radius is within 10% of a dimension of the second radius.

8. The method of claim 1, wherein the planned post-surgical alignment is determined by establishing an endpoint final post-surgical alignment and adding 15-25% to an angle representing the endpoint final post-surgical alignment, the angle being a function of the arc length and the second radius.

9. The method of claim 8, further comprising placing the rod intraoperatively, the elongate dimension of the rod being determined based on the planned post-surgical alignment, wherein the rod, once secured to the spine, is more closely aligned with the endpoint final post-surgical alignment than the planned post-surgical alignment.

10. The method of claim 1, wherein determining the first radius and the first position of the first circle involves aligning the first circle along a path passing through posterior sides of consecutive vertebrae of the spine.

11. The method of claim 1, wherein the first point is located at vertebra T1, T2, T3 or T4 and the second point is located at vertebra T12, L1 or L2.

12. The method of claim 1, wherein the pre-operative image captures the sagittal plane or the coronal plane.

13. The method of claim 1, wherein the pre-operative image is an x-ray image.

14. A method of preparing for a spine correction surgery that includes placement of a rod in a patient using a system with a processor and a memory and a rod forming machine, the method comprising:

identifying a segment of a spine of the patient requiring correction using an image of the spine stored in the memory, the segment including a first point along the spine at a first end of the segment and a second point along the spine at a second end of the segment;

determining a first radius and a first position of a first circle based on the image using the processor such that a portion of the first circle is generally aligned with a curve of the segment and the first circle passes adjacent to or through the first point and the second point;

based on a planned post-surgical spinal alignment, modifying the first circle to define a second circle using the processor, the second circle having a second radius different from the first radius and a second position based on the image such that the second circle passes adjacent to or through the first point and the second point, a portion of the second circle from the first point to the second point representing a modified post-surgical alignment of the segment adjusted to compensate for an expected loss of contour when the rod is attached to the spine;

measuring, by the processor, an angle between a first radial line extending between a center of the second circle and the first point and a second radial line extending between the center of the second circle and the second point;

using the angle and a radius of the second circle to determine a curvature and arc length of the segment having the modified post-surgical alignment; and forming a rod using the rod forming machine such that the rod has the determined curvature and arc length, the rod being ready for placement in a spine of a patient upon formation.

15. The method of claim 14, wherein the expected loss of contour is based on at least one of the material properties of the rod, the shape of the rod and a size of the rod.

16. The method of claim 14, wherein the expected loss of contour is in a range of 15% to 30% of the angle.

17. The method of claim 14, wherein determining the first radius and the first position of the first circle involves aligning the first circle along a path passing through posterior sides of consecutive vertebrae of the spine.

18. A method of forming a spinal rod comprising:

identifying a segment of a spine of a patient requiring correction using an image of the spine, the segment including a first point along the spine at a first end of the segment and a second point along the spine at a second end of the segment;

determining a first radius and a first position of a first circle based on the images such that a portion of the first circle generally aligns with a curve of the segment and the first circle passes adjacent to or through the first point and the second point;

modifying the first circle to define a second circle having a second radius different from the first radius and a second position based on the image such that the modified first circle passes adjacent to or through the first point and the second point, an arc length of the second circle extending along the second circle from the first point to the second point representing a post-surgical alignment of the segment; and forming the spinal rod to have a length based on the arc length of the second circle and a curvature based on the second radius of the second circle.

19. The method of claim 18, further comprising selecting a material for use in forming the spinal rod.

20. The method of claim 18, further comprising selecting a rod shape from the group consisting of a cylinder, a partial I-beam, and an omega shape.

* * * * *